(12) United States Patent
Seong et al.

(10) Patent No.: US 10,366,494 B2
(45) Date of Patent: Jul. 30, 2019

(54) IMAGE SEGMENTATION METHOD AND ELECTRONIC DEVICE THEREFOR

(71) Applicant: SAMSUNG ELECTRONICS CO., LTD., Suwon-si (KR)

(72) Inventors: Yeongkyeong Seong, Seoul (KR); Wonsik Kim, Gunpo-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 29 days.

(21) Appl. No.: 15/694,168

(22) Filed: Sep. 1, 2017

(65) Prior Publication Data

US 2018/0308237 A1  Oct. 25, 2018

(30) Foreign Application Priority Data

Apr. 21, 2017 (KR) .................. 10-2017-0051830

(51) Int. Cl.
*G06K 9/00* (2006.01)
*G06T 7/11* (2017.01)
(Continued)

(52) U.S. Cl.
CPC .............. *G06T 7/11* (2017.01); *G06F 19/321* (2013.01); *G06K 9/4604* (2013.01);
(Continued)

(58) Field of Classification Search
CPC ..... G06T 7/11; G06T 7/12; G06T 7/13; G06T 7/0012; G06T 7/0014; G06T 5/006; G06T 5/009; G06T 11/008; G06T 9/002; G06T 2207/10116; G06T 2207/10072; G06T 2207/10104; G06T 2207/10108;
(Continued)

(56) References Cited

U.S. PATENT DOCUMENTS 6,738,500 B2   5/2004  Bankman et al.
9,968,257 B1 *  5/2018  Burt .................... A61B 5/7267
(Continued)

FOREIGN PATENT DOCUMENTS

JP    5-282275 A    10/1993
JP    2004-97535 A   4/2004
(Continued)

OTHER PUBLICATIONS

Jonathan Long et al., "Fully Convolutional Networks for Semantic Segmentation", Publication date: Jun. 7, 2015, {jonlong,shelhamer,trevor}@cs.berkeley.edu, 10 pages total.

*Primary Examiner* — Jose L Couso
(74) *Attorney, Agent, or Firm* — Sughrue Mion, PLLC

(57) ABSTRACT

A computer-readable storage medium may be configured to store a program comprising instructions configured to, when executed by a computing device, cause the computing device to detect a selection of a partial area of the image, transform the image into a transformed image in which the selected partial area is positioned in a center of the transformed image, extract at least one feature from the transformed image, using a deep learning technique, enhance at least one feature of the at least one extracted feature, restore, as a restored image, at least one feature of the at least one enhanced feature, and inversely transform the restored image to provide segmented images.

22 Claims, 15 Drawing Sheets

(51) Int. Cl.

| | |
|---|---|
| *G06K 9/62* | (2006.01) |
| *G06K 9/46* | (2006.01) |
| *G06T 7/13* | (2017.01) |
| *G06T 7/00* | (2017.01) |
| *G06N 3/04* | (2006.01) |
| *G06F 19/00* | (2018.01) |
| *G06T 5/00* | (2006.01) |
| *G16H 50/20* | (2018.01) |
| *G16H 30/40* | (2018.01) |
| *A61B 6/00* | (2006.01) |
| *A61B 8/08* | (2006.01) |

(52) U.S. Cl.
CPC ......... *G06K 9/4628* (2013.01); *G06K 9/6253* (2013.01); *G06K 9/6256* (2013.01); *G06K 9/6267* (2013.01); *G06K 9/6271* (2013.01); *G06N 3/04* (2013.01); *G06T 5/006* (2013.01); *G06T 7/0014* (2013.01); *G06T 7/13* (2017.01); *G16H 30/40* (2018.01); *G16H 50/20* (2018.01); *A61B 6/5217* (2013.01); *A61B 8/5223* (2013.01); *G06K 2209/051* (2013.01); *G06T 2200/24* (2013.01); *G06T 2207/10081* (2013.01); *G06T 2207/10088* (2013.01); *G06T 2207/10132* (2013.01); *G06T 2207/20081* (2013.01); *G06T 2207/20084* (2013.01); *G06T 2207/20101* (2013.01); *G06T 2207/20132* (2013.01); *G06T 2207/30096* (2013.01)

(58) Field of Classification Search
CPC . G06T 2207/10132; G06T 2207/10081; G06T 2207/10088; G06T 2207/20101; G06T 2207/20016; G06T 2207/20081; G06T 2207/20084; G06T 2207/30061; G06T 2207/30068; G06T 2207/30096; G06T 2207/30016; G06T 2207/30064; G06T 2207/30101; G06T 2207/30168; G06N 3/04; G06N 3/08; G06N 3/0454; G06N 3/0445; G06N 3/084; G06N 99/005; G06F 19/00; G06F 19/321; G06F 19/36; G16H 50/20; G16H 30/20; G16H 30/40; G16H 40/40; G06K 9/4604; G06K 9/6256; G06K 9/6265; G06K 9/6267; G06K 9/6282; G06K 9/66; G06K 9/00442; G06K 9/3233; G06K 9/34; G06K 9/342; G06K 9/4676; G06K 2209/05; G06K 2209/051; G06K 2209/053; A61B 6/5217; A61B 6/5211; A61B 5/4887; A61B 5/7267; A61B 5/7485; A61B 5/0033; A61B 8/5223; A61B 2576/00; Y10S 128/922; Y10S 128/925; Y10S 706/924

See application file for complete search history.

(56) References Cited

U.S. PATENT DOCUMENTS

| | | | |
|---|---|---|---|
| 2013/0094725 | A1 | 4/2013 | Gulsun et al. |
| 2016/0174902 | A1* | 6/2016 | Georgescu ............... G06T 7/73 600/408 |
| 2016/0350919 | A1* | 12/2016 | Steigauf ............... G06T 7/0014 |
| 2017/0076451 | A1 | 3/2017 | Pauly |
| 2017/0083762 | A1 | 3/2017 | Segalovitz et al. |
| 2017/0169567 | A1* | 6/2017 | Chefd'hotel ....... G06K 9/00127 |
| 2017/0270664 | A1* | 9/2017 | Hoogi ...................... G06T 7/10 |
| 2017/0287137 | A1* | 10/2017 | Lin ......................... G06T 7/0081 |
| 2017/0337682 | A1* | 11/2017 | Liao ......................... G06T 7/30 |
| 2018/0033144 | A1* | 2/2018 | Risman ................... G06T 15/08 |
| 2018/0061046 | A1* | 3/2018 | Bozorgtabar ......... G06T 7/0012 |
| 2018/0061058 | A1* | 3/2018 | Xu ........................ G06K 9/6269 |
| 2018/0108139 | A1* | 4/2018 | Abramoff ................ G06T 7/11 |
| 2018/0144466 | A1* | 5/2018 | Hsieh ....................... G06N 3/04 |
| 2018/0259608 | A1* | 9/2018 | Golden ............. G01R 33/5608 |
| 2018/0330207 | A1* | 11/2018 | Zhou ................... G06K 9/6297 |

FOREIGN PATENT DOCUMENTS

| | | |
|---|---|---|
| KR | 10-2010-0096757 A | 9/2010 |
| KR | 10-2011-0037183 A | 4/2011 |

\* cited by examiner

IMAGE SEGMENTATION METHOD AND ELECTRONIC DEVICE THEREFOR

CROSS-REFERENCE TO RELATED APPLICATION

This application claims benefit from Korean Application Serial No. 10-2017-0051830, which was filed in the Korean Intellectual Property Office on Apr. 21, 2017, the entire content of which is incorporated herein by reference in its entirety.

TECHNICAL FIELD

Various exemplary embodiments of the present disclosure relate to an image segmentation method and an electronic device therefor.

BACKGROUND

Recently, a technology called deep learning developed in various fields. Particularly, a technology called a convolutional neural network (CNN), which is a kind of deep learning, has attracted attention in the field of object recognition. CNN is a model that simulates a person's brain function based on an assumption that, when a person recognizes an object, basic features of the object are extracted, a complicated calculation is performed inside the brain, and then the object is recognized based on a result of the calculation. In general, the CNN may use various filters for extracting a feature of an image through a convolution operation, a non-linear activation function (e.g., a sigmod function, a rectified linear unit (ReLU) function, etc.) or pooling for adding a non-linear characteristic, and the like.

Interest in deep learning has been increasing in the fields of various medical devices (e.g., ultrasound waves, computed tomography (CT), magnetic resonance imaging (MRI), etc.). For example, there is an increasing interest in analyzing a medical image (e.g., lesion search (or detect), feature extraction, boundary extraction, classification, etc.) by applying deep learning to a computer aided diagnosis (CAD) device.

SUMMARY

It may be desirable for the computer aided diagnosis device to correctly analyze an area (or region) of interest (e.g., lesion) of a medical image. For example, it may be desirable for the computer aided diagnosis device to accurately segment an area of interest of a medical image to correctly detect the boundary of the area of interest.

Therefore, recently, there is an increasing interest in a method for improving the accuracy of image segmentation in the computer aided diagnosis device.

Various exemplary embodiments of the present disclosure may perform image segmentation based on a point (e.g., a seed point) designated by a user.

Further, various exemplary embodiments of the present disclosure may perform image segmentation by enhancing (e.g., image enhancement and/or feature enhancement) an area (e.g., the center area of the screen) corresponding to the seed point.

According to an aspect of an exemplary embodiment, a computer-readable storage medium may be configured to store a program comprising instructions configured to, when executed by a computing device, cause the computing device to detect a selection of a partial area of the image, transform the image into a transformed image in which the selected partial area is positioned in a center of the transformed image, extract at least one feature from the transformed image, using a deep learning technique, enhance at least one feature of the at least one extracted feature, restore, as a restored image, at least one feature of the at least one enhanced feature, and inversely transform the restored image to provide segmented images.

The instructions may further cause the computing device to enhance the transformed image, and perform an image reverse enhancement of the restored image.

The instructions may further cause the computing device to downsize the image to prevent the image from being moved out of a display area when the image is transformed.

The instructions may further cause the computing device to trim a part from a display area of the image when the image is transformed, the part being generated by moving the image.

The instructions may further cause the computing device to extract the at least one feature by generating a feature map by applying a convolution function to the transformed image, reducing a size of the feature map by applying a pooling function to the feature map, and applying an activation function.

The instructions may further cause the computing device to enhance the at least one feature of the at least one extracted feature by adding a first classification result, in which the at least one extracted feature is classified, and a second classification result, in which the at least one extracted feature is classified by reducing a dimension of the at least one extracted feature.

The instructions may further cause the computing device to create a combined feature by combining the at least one extracted feature and at least one feature enhanced by spreading the at least one extracted feature, and determine a class of the combined feature.

The instructions may further cause the computing device to enhance the transformed image by enlarging the center of the transformed image.

The instructions may further cause the computing device to enhance the transformed image by performing image warping of the transformed image.

The instructions may further cause the computing device to extract a boundary based on the segmented images, and display the extracted boundary in the image.

The instructions may further cause the computing device to restore, as the restored image, the at least one enhanced feature and the at least one extracted feature.

According to another aspect of an exemplary embodiment, an image segmentation method includes acquiring an image, displaying the acquired image, detecting selection of a partial area of the acquired image, in response to detecting a selection of a partial area of the acquired image, transforming the acquired image into a transformed image in which the selected partial area is positioned in a center of the transformed image, extracting at least one feature from the transformed image, using a deep learning technique, enhancing at least one feature of the at least one extracted feature, restoring, as a restored image, at least one feature of the at least one enhanced feature, and inversely transforming the restored image to provide segmented images.

The transforming of the acquired image may further include one of reducing a size of the acquired image by trimming a part from a display area of the acquired image, the part being generated when the selected partial area is moved to the center of the transformed image, and downsizing the acquired image to prevent the acquired image from being moved out of the display area.

The extracting of the at least one feature may further include generating a feature map by applying a convolution function to the transformed image, reducing a size of the feature map by applying a pooling function to the feature map, and applying an activation function.

The enhancing of the at least one feature may further include a first classification operation comprising determining a class of the at least one extracted feature, a second classification operation comprising reducing a dimension of the at least one extracted feature and determining a class of the dimension-reduced feature, and adding a result of the first classification operation and a result of the second classification operation.

The enhancing of the at least one feature may further include creating a combined feature by combining the at least one extracted feature and at least one feature enhanced by spreading the at least one extracted feature, and determining a class of the combined feature.

The method may further include enhancing the transformed image, and performing an image reverse enhancement of the restored image.

The enhancing of the transformed image may further include enlarging the center of the transformed image.

The enhancing of the transformed image may further include performing image warping of the transformed image.

The method of claim 12 may further include extracting a boundary based on the segmented images, and displaying the extracted boundary in the acquired image.

The restoring may further include restoring, as the restored image, the at least one enhanced feature and the at least one extracted feature.

According to another aspect of an exemplary embodiment, An electronic device includes a display configured to display an image, at least one processor operatively connected to the display, and a memory operatively connected to the at least one processor, wherein the memory is configured to store instructions which, when executed, cause the processor to, in response to detecting a selection of a partial area of a displayed image, extract at least one feature from the displayed image, using a deep learning technique, enhance at least one feature corresponding to the partial area of the at least one extracted feature, and restore, as a restored image, at least one feature of the enhanced feature to provide segmented images.

The deep learning technique may include applying at least one from among a restricted Boltzmann machine, a deep belief network, a deep neural network, and a convolutional neural network.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION

Figure 1:
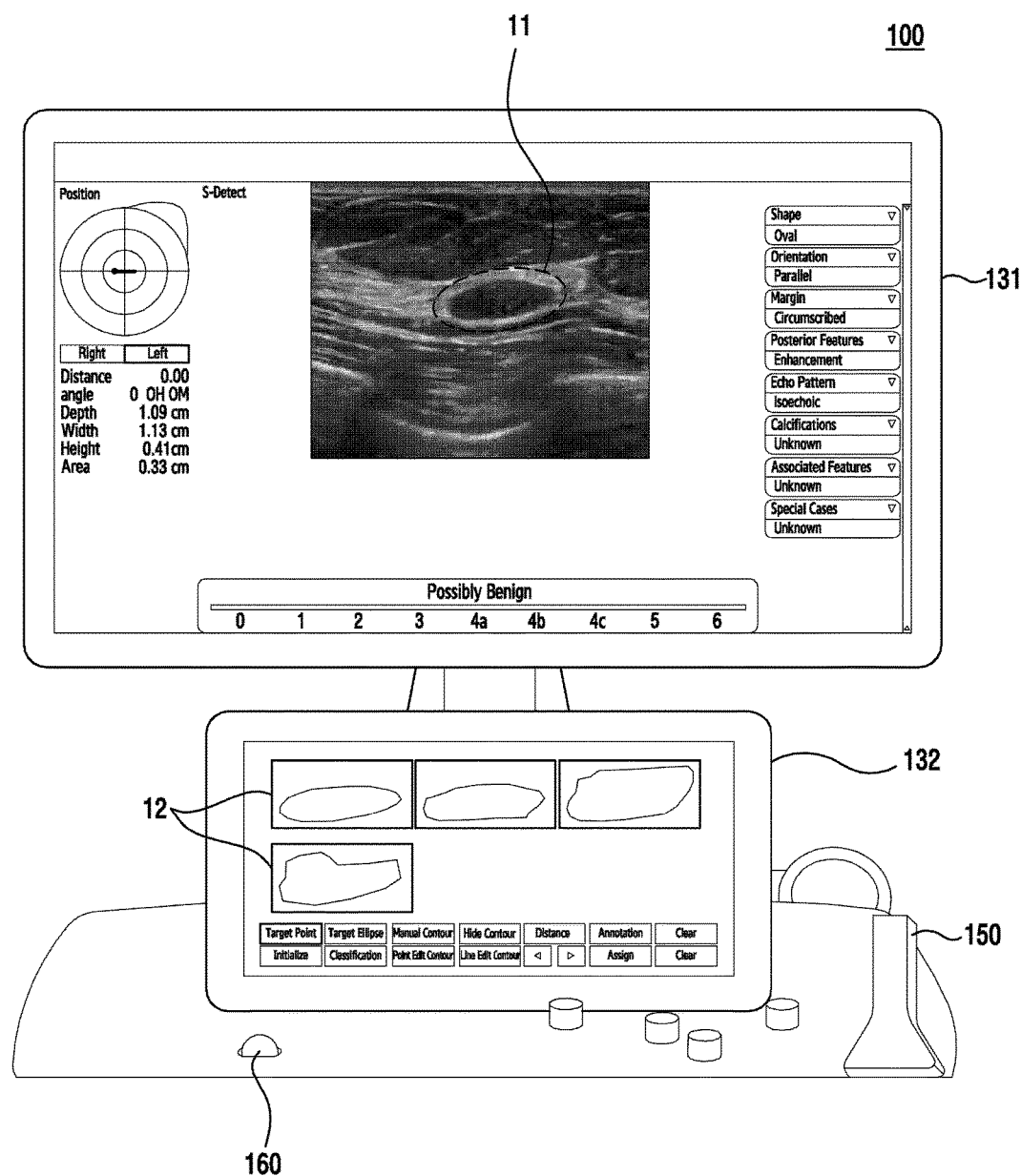
FIG. 1 is a diagram illustrating an electronic device according to an exemplary embodiment.

Various example embodiments are described in greater detail with reference to the accompanying drawings. The same or similar components may be designated by the same or similar reference numerals although they are illustrated in different drawings. Detailed descriptions of constructions or processes known in the art may be omitted to avoid obscuring the subject matter of the present disclosure.

The terms used herein are used in consideration of functions of the present disclosure and may vary depending on a user's or an operator's intention and usage. Therefore, the terms used herein should be understood based on the descriptions made herein. It is to be understood that the singular forms "a," "an," and "the" include plural referents unless the context clearly dictates otherwise. In the present disclosure, an expression such as "A or B," "at least one of A and B," or "one or more of A and B" may include all possible combinations of the listed items. Expressions such as "first," "second," "primarily," or "secondary," as used herein, may represent various elements regardless of order and/or importance, and do not limit corresponding elements. The expressions may be used for distinguishing one element from another element. When it is described that an element (such as a first element) is operatively or communicatively "coupled to" or "connected to" another element (such as a second element), the element can be directly connected to the other element or can be connected through another element (such as a third element).

The expression "configured to (or set)", as used in the present disclosure, may be used interchangeably with, for example, "suitable for," "having the capacity to," "designed to," "adapted to," "made to," or "capable of" according to the situation. The term "configured to (or set)" does not only refer to "specifically designed to" by hardware. Alternatively, in some situations, the expression "apparatus configured to" may refer to a situation in which the apparatus "can" operate together with another apparatus or component. For example, the phrase "a processor configured (or set) to perform A, B, and C" may be, for example, and without limitation, a dedicated processor, a generic-purpose processor (such as a central processing (CPU) or an application processor (AP)) that can perform a corresponding operation by executing at least one software program stored at an exclusive processor (such as an embedded processor) for performing a corresponding operation or at a memory device.

An electronic device, according to exemplary embodiments of the present disclosure, may be embodied as, for example, at least one of various medical devices (e.g., a magnetic resonance angiography (MRA) device, a magnetic resonance imaging (MRI) device, a computed tomography (CT) device, a X-ray device, and an ultrasonic wave device, or the like), but is not limited thereto.

An electronic device is not limited to the foregoing devices may be embodied as a newly developed electronic device. The term "user", as used herein, can refer to a person using an electronic device or a device using an electronic device (e.g., an artificial intelligence electronic device).

Prior to the detailed description, the terms used in the present document are briefly described, and various exemplary embodiments are described in detail. Although currently and widely used general terms have been selected for the terms used in the present document while considering technical features according to various exemplary embodiments, the selected terms may vary depending on the intention of those skilled in the art to which the present disclosure belongs, precedent cases, the emergence of new technologies, or the like. Further, in a case where a term is arbitrarily selected by the applicant, the meaning thereof will be described in detail in a corresponding description part of the present document. Therefore, the term used in the present document should be defined based on the meaning of the term and the overall content of the present document, and should not be defined merely based on the expression of the term.

In the present document, "an image" may refer to multi-dimensional data including discrete image elements (for example, pixels in a two-dimensional image and voxels in a three-dimensional image). For example, the image may include a medical image of an object, which is acquired by X-ray, computed tomography (CT), magnetic resonance imaging (MRI), ultrasound waves, and other medical imaging systems.

Further, in the present document, the "object" may include a person or an animal, or a part of a person or a part of an animal. For example, the object may include an organ (e.g., a liver, a heart, a uterus, a brain, a breast, an abdomen, etc.), a blood vessel, a lesion, and/or the like.

Further, in the present document, a "user" may be, as a medical professional, a doctor, a nurse, a clinical pathologist, a medical imaging specialist, etc., and may also be a technician who repairs a medical device. However, the user may not be limited thereto.

At least one of the components, elements, modules or units represented by a block as illustrated in the drawings, may be embodied as various numbers of hardware, software and/or firmware structures that execute respective functions described above, according to an exemplary embodiment. For example, at least one of these components, elements, modules or units may use a direct circuit structure, such as a memory, a processor, a logic circuit, a look-up table, etc. that may execute the respective functions through controls of one or more microprocessors or other control apparatuses. Also, at least one of these components, elements, modules or units may be specifically embodied by a module, a program, or a part of code, which contains one or more executable instructions for performing specified logic functions, and executed by one or more microprocessors or other control apparatuses.

Also, at least one of these components, elements, modules or units may further include or may be implemented by a processor such as a central processing unit (CPU) that performs the respective functions, a microprocessor, or the like. Two or more of these components, elements, modules or units may be combined into one single component, element, module or unit which performs all operations or functions of the combined two or more components, elements, modules or units. Also, at least part of functions of at least one of these components, elements, modules or units may be performed by another of these components, elements, modules or units. Further, although a bus is not illustrated in the above block diagrams, communication between the components, elements, modules or units may be performed through the bus. Functional aspects of the above exemplary embodiments may be implemented in algorithms that execute on one or more processors. Furthermore, the components, elements, modules or units represented by a block or processing steps may employ any number of related art techniques for electronics configuration, signal processing and/or control, data processing and the like.

Various exemplary embodiments described hereinafter are associated with an image segmentation device that can segment an image through machine learning. For example, an image segmentation device according to various exemplary embodiments may segment an image using various deep learning algorithms (e.g., a restricted Boltzmann machine (RBM), a deep belief network (DBN), a deep neural network (DNN), a convolutional neural network (CNN), etc.). Hereinafter, a case of using the CNN algorithm will be described as an example for convenience of explanation.

An image segmentation module according to various exemplary embodiments may be included in an electronic device (e.g., a computer aided diagnosis (CAD) device, an image processing device, a personal computer, a server, etc.). Alternatively, an image segmentation device may be included in an external device (e.g., an external memory, an external electronic device, or an external server, etc.) connected with the electronic device through a wire or wirelessly. Hereinafter, a case where the image segmentation module is included in a computer aided diagnosis device will be described as an example.

FIG. 1 is a diagram illustrating an electronic device according to an exemplary embodiment.

Referring to FIG. 1, an electronic device 100 according to an exemplary embodiment may acquire at least one image by photographing an object (e.g., inside of a patient's body). For example, the electronic device 100 may be an ultrasound diagnosis device including a computer aided diagnosis device. According to an exemplary embodiment, the electronic device 100 may be a CT device, an MRI device, and an X-ray photographing device.

The electronic device 100 may acquire an image through a probe 150 in real time, and display the acquired image on at least a partial area of a first display 131 and/or a partial area of a second display 132. The electronic device 100 may analyze the acquired image. For example, when a point or an area of the image displayed on the second display 132 is selected using a touch or a pointing device (e.g., a trackball 160), the electronic device 100 may detect an area (or region) of interest (e.g., a lesion area) from the displayed image, and graphically provide (e.g., display) a boundary 11 of the detected area of interest to the image displayed on the first display 131. In addition, the electronic device 100 may provide one or more boundary candidates 12 of the area of interest on the second display 132. When one of the boundary candidates 12 of the area of interest is selected, the electronic device 100 may change the boundary 11 of the area of interest using the selected boundary candidate of the area of interest.

In order to extract the boundary of the area of interest, the electronic device 100 may segment the image through a deep learning technique. For example, the electronic device 100 may segment the image using convolutional neural network (CNN)-based fully convolutional networks (FCN).

The electronic device 100 according to various exemplary embodiments may segment the image around a specific point (hereinafter, referred to as a seed point) of the image, which is designated (or selected) by a user. For example, the electronic device 100 may be able to improve accuracy of image segmentation by transforming the image (e.g., moving a location and changing a size (resizing)) such that the seed point becomes the center of the image, extracting at least one feature from the transformed image; and enhancing the extracted feature (e.g., enhancing a feature of the center area). A detailed description thereof will be provided later with reference to FIG. 3A and FIG. 5.

According to an exemplary embodiment, the electronic device 100 may further perform image enhancement for enhancing the transformed image, and reverse enhancement of the image. For example, the electronic device 100 may perform image enhancement (e.g., image warping for enlarging the center area of the image) of the transformed image after an image transformation. Further, the electronic device 100 may perform reverse enhancement of the image, which restores the enhanced image. A detailed description thereof will be provided later with reference to FIG. 3B and FIG. 6.

According to an exemplary embodiment, the electronic device 100 may perform image enhancement and feature enhancement around a selected point of the image, instead of performing image enhancement and feature enhancement around the center of the image. In this case, the electronic device 100 may not perform an image transformation and an inverse transformation of the image. A detailed description thereof will be provided later with reference to FIG. 3C, FIG. 3D, and FIG. 7.

Figure 2:
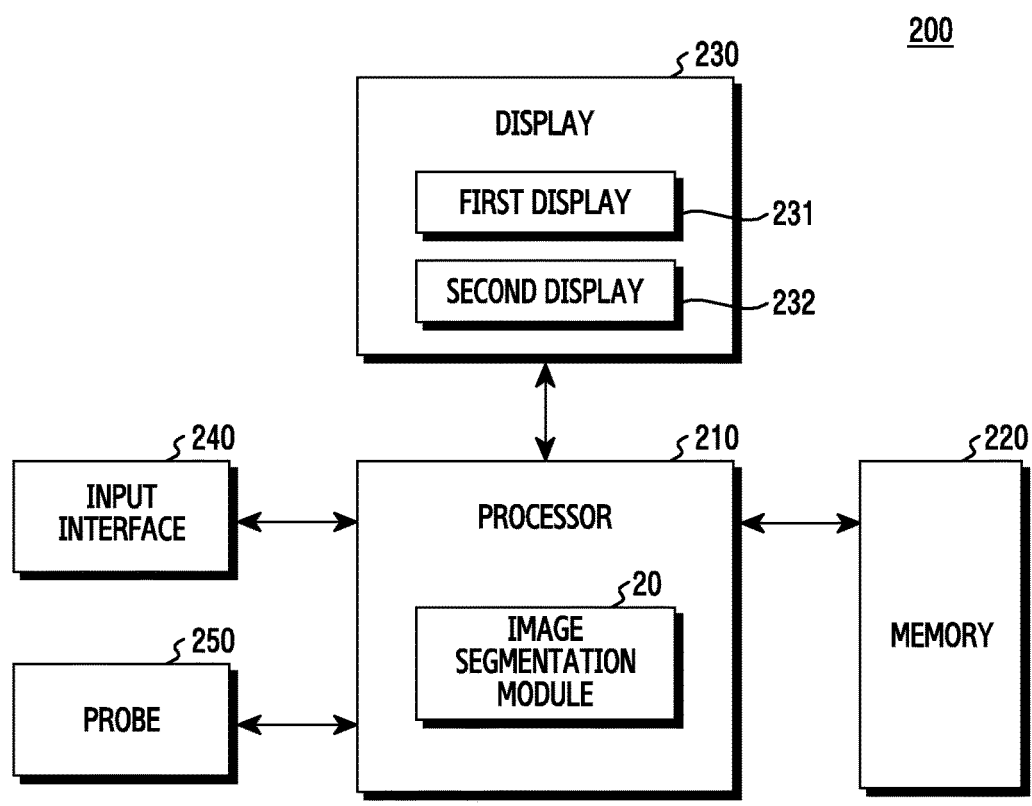
FIG. 2 is a block diagram illustrating a configuration of an electronic device according to an exemplary embodiment.

FIG. 2 is a block diagram illustrating configuration of an electronic device according to an exemplary embodiment.

Referring to FIG. 2, an electronic device 200 (e.g., the electronic device 100 of FIG. 1) according to an exemplary embodiment may include a processor 210, a memory 220, a display 230, an input interface 240, and a probe 250.

The processor 210 may control an overall operation of the electronic device 200. For example, the processor 210 may be electrically (or operatively) connected with the memory 220, the display 230, the input interface 240, and the probe 250 so as to control each of elements of the electronic device 200.

The processor 210 may receive a command or instructions from the memory 220, control each of elements according to the received command or instructions, and perform various functions. The processor 210 may be formed of a central processing unit (CPU), an application processor (AP), a micro control unit (MCU), a microprocessor unit (MCU), and the like. The processor 210 may be formed of a single core processor or a multi-core processor. In another exemplary embodiment, the processor 210 may be a multi-processor including a plurality of processors. In still another exemplary embodiment, the processor 210 may further include a graphic processing unit (GPU) and/or an image signal processor. According to still another exemplary embodiment, the processor 210 may be formed of a GPU or an image signal processor.

The processor 210 according to various exemplary embodiments may segment an image selected by a user, using deep learning around a specific point (or area) of the image. For example, the processor 210 may transform the image such that the specific point of the image is positioned near the center, and extract a feature of the image by applying deep learning to the transformed image. In addition, the processor 210 may enhance the extracted feature of the image. For example, the processor 210 may enhance a feature of the center area of the image. The processor 210 may increase the size of the image (e.g., increasing a resolution) by enhancing the feature and then performing a resize to the original size (e.g., upsampling, deconvolution, or the like). The processor 210 may perform an inverse transformation of the size-increased image. For example, the processor 210 may restore the position of the specific point (or area), which has been moved to near the center of the image, to a position before the movement.

According to an exemplary embodiment, the processor 210 may perform image enhancement of the transformed image. The image enhancement may be an operation of modifying the size of the image such that a point closer to the center of the image has a higher resolution. For example, the processor 210 may perform image enhancement using a log polar transformation. A detailed description thereof will be provided later with reference to FIG. 4E. However, various exemplary embodiments are not limited to performing of the image enhancement through the log polar transformation, and various image enhancement techniques may be applied. The processor 210 may perform a resize to the original size, and then perform reverse enhancement of the image. For example, the processor 210 may perform a backward transformation.

The processor 210 for performing the above described operations may include an image segmentation module 20. According to an exemplary embodiment, the image segmentation module 20 may be stored as a software module in the memory 220. A detailed description of the image segmentation module 20 will be provided later with reference to FIG. 3A to FIG. 3D.

The processor 210 may analyze a medical image (e.g., an ultrasound image). For example, the processor 210 may detect a lesion from the medical image, extract a boundary of the detected lesion based on a segmentation result of the image, and display the extracted boundary of the lesion in the medical image (e.g., an original image). Further, the processor 210 may display a diagnosis result of the detected lesion in an area of the display 230.

The memory 220 may be electrically (or operatively) connected with the processor 210. The memory 220 may store various programs for operating the electronic device 200, and store data generated in the middle of performing the various programs, downloaded data, or the like. Further, the memory 220 may store various commands and/or instructions for operating the processor 210. The memory

220 may include at least one of an embedded memory and an external memory. The embedded memory may include at least one of a volatile memory (e.g., DRAM, SRAM, SDRAM, or the like), a non-volatile memory (e.g., one time programmable ROM (OTPROM)), a PROM, an EPROM, an EEPROM, a mask ROM, a flash ROM, a flash memory, a hard drive, and a solid-state drive (SSD). The external memory may include a flash drive, which can be functionally or physically connected with the electronic device 200 through various interfaces, for example, a compact flash (CF) memory, a secure digital (SD) memory, a micro-SD memory, a mini-SD memory, an extreme digital (xD) memory, a multi-media card (MMC) memory, and a universal serial bus (USB) type memory or a memory stick.

The memory 220 may store an analysis program that analyzes an image (e.g., lesion detection, image segmentation, boundary extraction, diagnosis, etc.). For example, the analysis program may detect a lesion from a medical image, extract a boundary of the lesion through image segmentation, and diagnose the lesion (e.g., diagnosing whether the lesion is malignant or benign) in consideration of the shape, texture, direction, etc. of the extracted boundary of the lesion. According to an exemplary embodiment, the analysis program may determine a grade (or level) of the lesion. For example, the analysis program may classify the lesion into various grades based on the possibility of the lesion being benign or malignant. Further, the analysis program may calculate and provide a reliability of a diagnosis result on whether the lesion is malignant or benign.

According to various exemplary embodiments, the memory 220 may store a learning database (DB) for image segmentation generated by learning a plurality of medical images through a deep learning technique. Alternatively, the learning DB may be stored in an external device (e.g., an external memory, an external server, etc.).

The display 230 may provide an input function and/or an output function. For example, the display 230 may include a touch panel and/or a display panel. The display panel may be formed of, for example, a liquid crystal display (LCD), a light emitting diode (LED) display, an organic light emitting diode (OLED) display, a micro-electro-mechanical system (MEMS) display, or an electronic paper display. The touch panel may detect (or recognize) a change in physical characteristics (capacitance, frequency, etc.) caused by various touch inputs (e.g., tap, double tap, touch, touch movement, multi-touch, pressure touch, or the like) using an input tool, such as a finger, a stylus, and an electronic pen, and transfer the detected change to the processor 210. The touch panel may include a first panel (not illustrated) that detects a touch using a finger, a second panel (not illustrated) for electronic pen recognition, and/or a third panel (not illustrated) for pressure detection.

The display 230 according to various exemplary embodiments may include a first display 231 and a second display 232. For example, the first display 231 and the second display 232 may provide an input function and/or an output function. The second display 232 may be detachably attached to the electronic device 200. The second display 232 may receive a user input that designates a point or an area in a medical image.

In FIG. 2, the display 230 has been described to include two displays. However, according to an exemplary embodiment, the display 230 may include one display, or two or more display.

The input interface 240 may include a key, and/or a pointing device. The key may include, for example, a physical button, an optical key, or a keypad. The pointing device may include a mouse, a touch pad, a joystick, a trackball, and the like. The input interface 240 according to various exemplary embodiments may receive a user input that designates an area from which a boundary is to be detected. When the input interface 240 is formed as a touch panel, the input interface 240 may be integrated with the display 230, for example, the first display 231 and/or the second display 232.

The probe 250 may acquire a medical image of a patient. Here, the medical image may be an ultrasound image acquired through the probe 250 in frame units in real time.

The probe 250 may simultaneously or sequentially transmit an ultrasound signal to an object in multiple directions, and receive an ultrasound echo signal of each ultrasound signal, which is reflected from the object. The electronic device 200 may determine the number of transmission directions of the ultrasound signal of the probe 250, the transmission directions of the ultrasound signal, and energy of the ultrasound signal.

In the above description, it has been described that the electronic device 200 acquires an image through the probe. However, according to an exemplary embodiment, the electronic device 200 may acquire an image by downloading or reading a medical image stored in an external device. The external device may be an external memory connected with the electronic device 200, or an external electronic device or an external server, which is connected with the electronic device 200 through a wire and/or wirelessly. Alternatively, the medical image may be a slice image set acquired in three dimensions through a computed tomography (CT) device, a magnetic resonance imaging (MRI) device, and the like. Each slice image of the slice image set may correspond to each frame image.

According to an exemplary embodiment, when an external device includes an image segmentation module, the electronic device 200 may transmit an acquired image to the external device, and receive a segmentation result from the external device.

The electronic device 200 may not include some of the described elements. For example, when the electronic device 200 is a CT device or an MRI device, the electronic device 200 may not include the probe 250. According to another exemplary embodiment, the electronic device 200 may further include at least one other element (e.g., a communication module, a boundary extraction module, a diagnosis module, etc.) at a level equivalent to that of the described elements.

An electronic device (e.g., the electronic device 100, or the electronic device 200) according to various example embodiments may comprise: a display (e.g., the display 131 and 132, or the display 230) configured to display an image; at least one processor (e.g., the processor 210) operatively connected with the display; and a memory (e.g., the memory 220) operatively connected with the at least one processor, wherein the memory is configured to store instructions configured to, when executed, cause the processor to: transform the image such that a selected partial area of the image is positioned in the center of the image, in response to detection of selection of the partial area; extract at least one feature from the transformed image, using deep learning; enhance at least one feature of the at least one extracted feature; restore, as an image, at least one feature of the at least one enhanced feature; and inversely transform the restored image to provide segmented images.

According to various exemplary embodiments, the memory is configured to further store: an instruction configured to, when executed, cause the processor to enhance the transformed image; and an instruction configured to, when executed, cause the processor to perform an image reverse enhancement of the restored image.

According to various exemplary embodiments, the instructions are configured to cause the processor to downsize the moved image to prevent the image from being out of a display area thereof when the image is transformed.

According to various exemplary embodiments, the instructions are configured to cause the processor to trim a part out of a display area of the image when the image is transformed, the part being generated by moving of the image.

According to various exemplary embodiments, the instructions are configured to cause the processor to repeat a predetermined number of times: generation of a feature map by applying a convolution function to the transformed image, reduction of the size of the feature map by applying a pooling function to the feature map, and application of an activation function, so as to extract the at least one feature.

According to various exemplary embodiments, the instructions are configured to cause the processor to add a first classification result, in which the at least one extracted feature is classified, and a second classification result, in which the at least one extracted feature is classified by reducing a dimension thereof, so as to enhance the at least one feature.

According to various exemplary embodiments, the instructions are configured to cause the processor to combine the at least one extracted feature and at least one feature enhanced by spreading the at least one extracted feature, and to classify a class of the combined feature.

According to various exemplary embodiments, the instructions are configured to cause the processor to enhance the image by enlarging the center of the transformed image.

According to various exemplary embodiments, the instructions are configured to cause the processor to enhance the image by performing image warping of the transformed image.

According to various exemplary embodiments, the memory is configured to further store instructions configured to, when executed, cause the processor to extract a boundary based on the segmented images, and to display the extracted boundary in the acquired image.

According to various exemplary embodiments, the instructions are configured to cause the processor to restore, as an image, at least one of the at least one enhanced feature and at least one of the at least one extracted feature.

An electronic device (e.g., the electronic device 100, or the electronic device 200) according to various example embodiments may comprise: a display configured to display an image; at least one processor operatively connected to the display; and a memory operatively connected to the at least one processor, wherein the memory is configured to store instructions which, when executed, cause the processor to: in response to detecting a selection of a partial area of the displayed image, extract at least one feature from the displayed image, using a deep learning technique; enhance at least one feature corresponding to the partial area of the at least one extracted feature; restore, as a restored image, at least one feature of the at least one enhanced feature to provide segmented images.

Figure 3A:
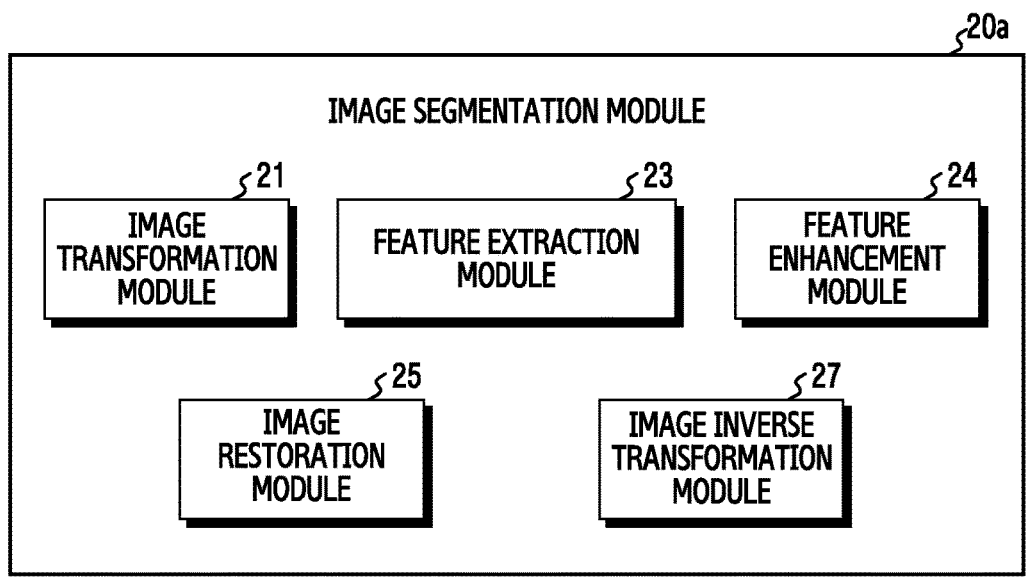
FIG. 3A is a block diagram illustrating a configuration of an image segmentation module of an electronic device according to an exemplary embodiment.

FIG. 3A is a block diagram illustrating a configuration of an image segmentation module of an electronic device according to an exemplary embodiment.

Referring to FIG. 3A, an image segmentation module 20a of an electronic device (e.g., the electronic device 100 of FIG. 1 and the electronic device 200 of FIG. 2) according to an exemplary embodiment may include an image transformation module 21, a feature extraction module 23, a feature enhancement module 24, an image restoration module 25, and an image inverse transformation module 27.

The image transformation module 21 may transform the size and position of an image. According to various exemplary embodiments, the image transformation module 21 may move an image such that a point designated by a user becomes the center of the image. For example, when a user selects (e.g., touches) a point that is positioned a distance of 100 (e.g., pixels) from the center to the upper side of the image, and a distance of 30 (e.g., pixels) from the center to the left side of the image, the image transformation module 21 may move the image a distance of 100 (e.g., pixels) to the lower side and a distance of 30 to the right side. In response to the movement, the image transformation module 21 may trim the image by a distance of 100 (e.g., pixels) from the bottom edge of the image, and may trim the image by a distance of 30 (e.g., pixels) from the right edge thereof. According to an exemplary embodiment, the moved image may be resized (e.g., downsized) to prevent the image from being trimmed.

The feature extraction module 23 may extract various features of the image. According to various exemplary embodiments, the feature extraction module 23 may extract at least one feature from the image, using a deep learning algorithm. For example, the feature extraction module 23 may extract a feature of the image using a convolutional neural network (CNN). The convolutional neural network may have a multi-layer structure, and each layer may include a convolution layer, a pooling layer, and an activation function layer.

The convolution layer may generate a feature map that expresses various features of the image, by performing a convolution operation for the image using a convolution filter. The pooling layer may reduce the size of the feature map. The pooling layer may be referred to as subsampling. The activation function layer may be a non-linear function, such as a rectified linear unit (ReLU) function, a sigmod function, and the like.

The feature enhancement module 24 may enhance at least one of the extracted features and classify a class thereof by combining the features. For example, the feature enhancement module 24 may enhance at least one feature (e.g., a feature of the center part of the image) of at least one of the extracted features, and perform classification into classes by combining the extracted features. Accordingly, since the image transformation module 21 has moved the point or area selected by the user to the center of the image, the feature enhancement module 24 may enhance a feature of the point or area selected by the user. The detailed description of the feature enhancement module 24 will be provided later with reference to FIG. 4A to FIG. 4D.

The image restoration module 25 may restore at least one of the at least one enhanced feature into an image. Alternatively, the image restoration module 25 may restore an image using at least one of the at least one enhanced feature and at least one of the at least one extracted feature. The image restoration module 25 may enlarge (restore) the feature map to its original size by performing upsampling, the size of the feature map having been reduced by the convolution layer and the pooling layer. According to an exemplary embodiment, the image restoration module 25 may restore the image using various known techniques, such as unpooling or deconvolution.

The image inverse transformation module 27 may retransform (or inversely transform) the image restored by the image restoration module 25, such that the image has the size and/or position before being transformed by the image transformation module 21. For example, when the image transformation module 21 has moved the image a distance of 100 (e.g., pixels) to the lower side and a distance of 30 (e.g., pixels) to the right side, the image inverse transformation module 27 may perform inverse transformation by moving the image a distance of 100 (e.g., pixels) to the upper side and a distance of 30 (e.g., pixels) to the left side. The image inverse transformation module 27 may restore a part of the image, which has been trimmed when the image was transformed (the image trimmed by a distance of 100 (e.g., pixels) from the bottom edge thereof, and the image trimmed by a distance of 30 (e.g., pixels) from the right edge thereof). According to an exemplary embodiment, the image inverse transformation module 27 may enlarge the image by a ratio of reduction performed by the image transformation module 21, and may perform an inverse transformation by moving the image in an opposite direction as much as the distance of movement made by the image transformation module 21.

Figure 3B:
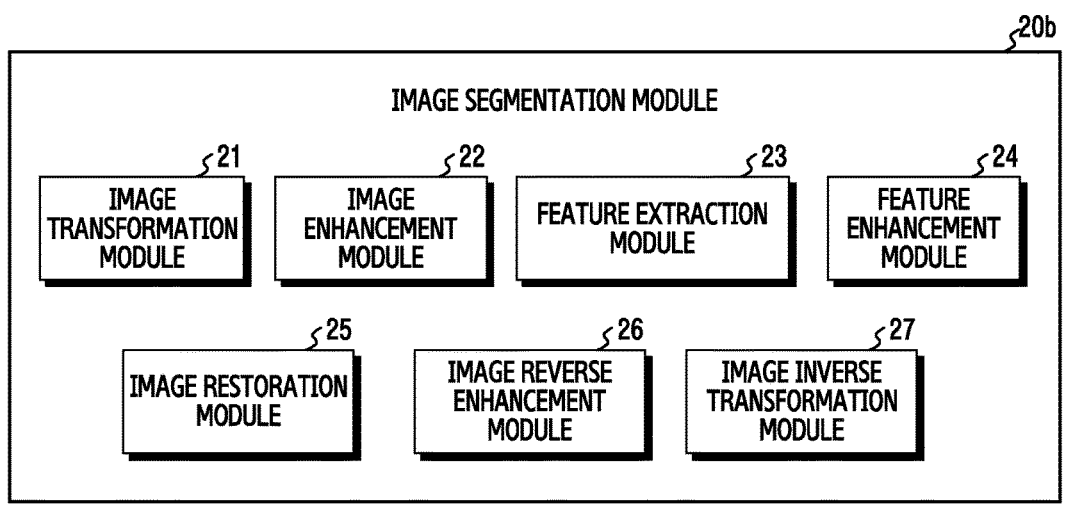
FIG. 3B is a block diagram illustrating a configuration of an image segmentation module of an electronic device according to another exemplary embodiment.

FIG. 3B is a block diagram illustrating a configuration of an image segmentation module of an electronic device according to another exemplary embodiment.

Referring to FIG. 3B, an image segmentation module 20b of the electronic device (e.g., the electronic device 100 of FIG. 1, and the electronic device 200 of FIG. 2) according to another exemplary embodiment may include the image transformation module 21, an image enhancement module 22, the feature extraction module 23, the feature enhancement module 24, the image restoration module 25, an image reverse enhancement module 26, and the image inverse transformation module 27.

According to another exemplary embodiment, the image segmentation module 20b may further include the image enhancement module 22 and the image reverse enhancement module 26. The image transformation module 21, the feature extraction module 23, the feature enhancement module 24, the image restoration module 25, and the image inverse transformation module 27 according to another exemplary embodiment may operate in a manner similar to those of FIG. 3A. A detailed description thereof will be omitted.

The image enhancement module 22 may enhance an image, the size and position of which have been transformed by the image transformation module 21. For example, the image enhancement module 22 may enlarge a point (or an area) designated by a user. According to an exemplary embodiment, the image enhancement module 22 may enhance the image using a log polar transform. For example, the image enhancement module 22 may modify the size of the image such that the center area of the transformed image has a relatively high resolution. A detailed description thereof will be provided later with reference to FIG. 4E. However, various exemplary embodiments are not limited thereto, and various known techniques may be used.

The image reverse enhancement module 26 may restore the image modified by the image enhancement module 22 by reversely enhancing an image restored by the image restoration module 25.

Figure 3C:
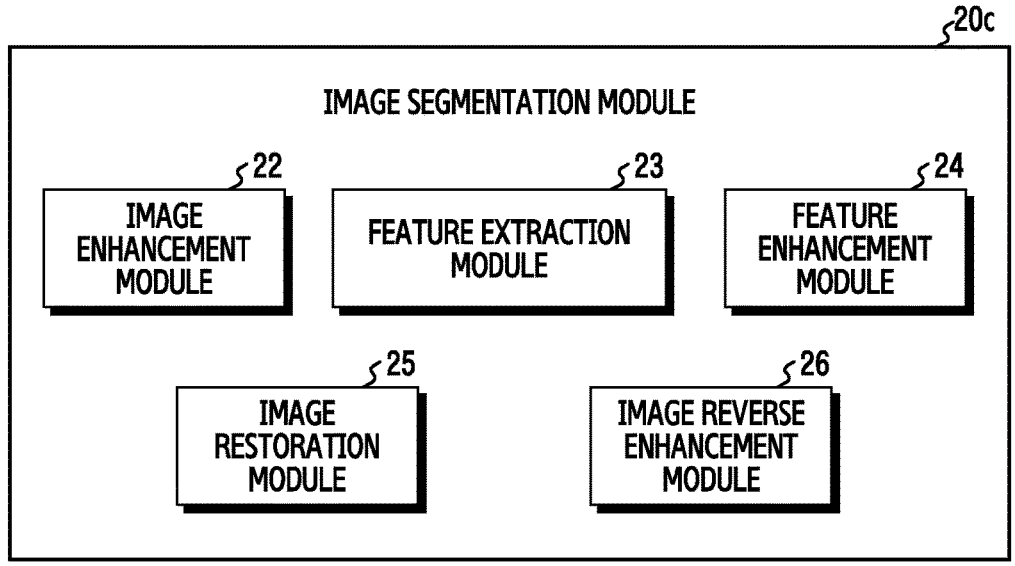
FIG. 3C is a block diagram illustrating a configuration of an image segmentation module of an electronic device according to still another exemplary embodiment.

FIG. 3C is a block diagram illustrating a configuration of an image segmentation module of an electronic device according to still another exemplary embodiment.

Referring to FIG. 3C, an image segmentation module 20c of the electronic device (e.g., the electronic device 100 of FIG. 1, and the electronic device 200 of FIG. 2) according to still another exemplary embodiment may include the image enhancement module 22, the feature extraction module 23, the feature enhancement module 24, the image restoration module 25, and the image reverse enhancement module 26.

According to still another exemplary embodiment, the image segmentation module 20c of FIG. 3C may not include the image transformation module 21 that moves a point or area designated by a user to the center of an image, and the image inverse transformation module 27 that restores the movement.

The image enhancement module 22 may enhance a part of the image, which includes the point or area designated by the user, instead of enhancing the center area of the image. Similarly, the feature enhancement module 24 may enhance a feature of the area including the point or area designated by the user. The feature extraction module 23, the image restoration module 25, and the image reverse enhancement module 26 may operate in a manner similar to those of FIG. 3A and FIG. 3B. A detailed description thereof will be omitted.

Figure 3D:
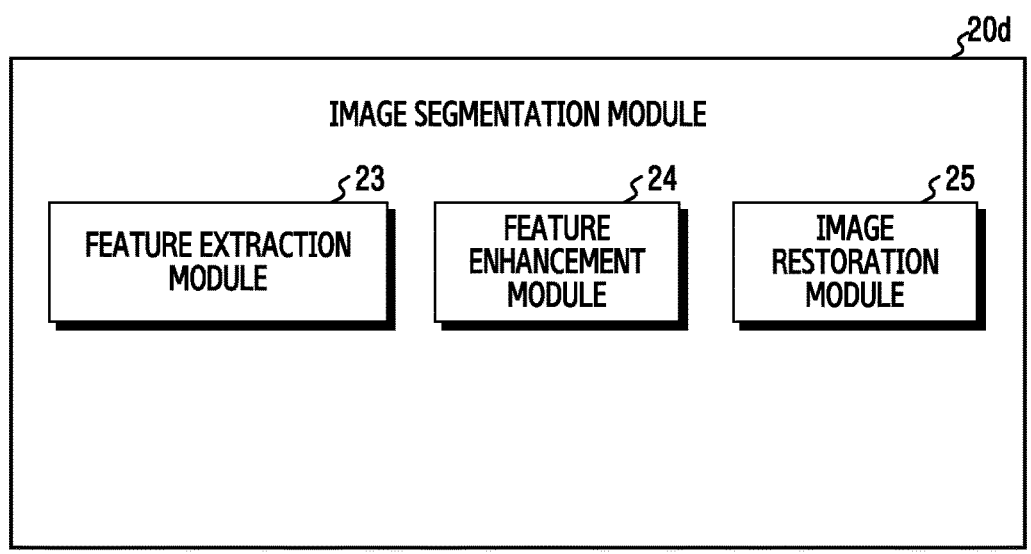
FIG. 3D is a block diagram illustrating a configuration of an image segmentation module of an electronic device according to still another exemplary embodiment.

FIG. 3D is a block diagram illustrating a configuration of an image segmentation module of an electronic device according to still another exemplary embodiment.

Referring to FIG. 3D, an image segmentation module 20d of the electronic device (e.g., the electronic device 100 of FIG. 1, and the electronic device 200 of FIG. 2) according to still another exemplary embodiment may include the feature extraction module 23, the feature enhancement module 24, and the image restoration module 25.

The image segmentation module 20d according to still another exemplary embodiment may correspond to the image segmentation module 20c of FIG. 3C, in which the image enhancement module 22 and the image reverse enhancement module 26 are excluded. The feature extraction module 23, the feature enhancement module 24, and the image restoration module 25 may operate in a manner similar to those of FIG. 3C. For example, when a user designates a specific point or area of an image, the image segmentation module 20d may extract a feature of the image using the feature extraction module 23, enhance a feature of an area, which includes the point or area having been designated by the user, using the feature enhancement module 24, and restore the extracted feature, which includes the enhanced feature, as an image using the image restoration module 25.

Figure 4A:
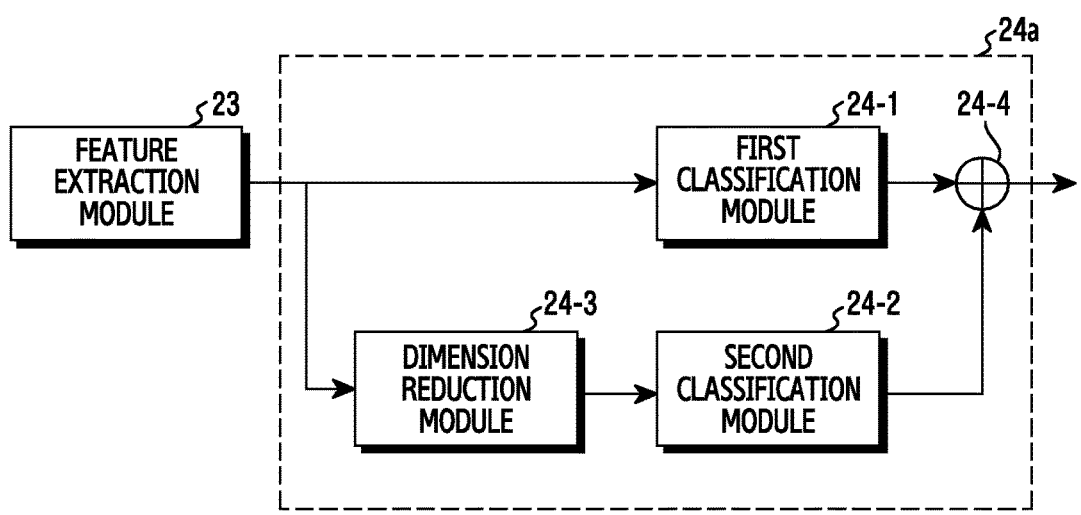
FIG. 4A is a block diagram illustrating a configuration of a feature enhancement module of an electronic device according to an exemplary embodiment.

FIG. 4A is a block diagram illustrating a configuration of a feature enhancement module of an electronic device according to an exemplary embodiment.

Referring to FIG. 4A, a feature enhancement module 24a according to an exemplary embodiment may include a first classification module (classifier) 24-1, a second classification module 24-2, a dimension reduction module 24-3, and an adder 24-4.

The dimension reduction module 24-3 may reduce a dimension. For example, the dimension reduction module 24-3 may reduce a dimension by expressing a feature through an association rule between data. The dimension reduction module 24-3 according to an exemplary embodiment may reduce a dimension by selecting a meaningful feature among features extracted by the feature extraction module 23. For example, in the exemplary embodiments, since the point or area designated by the user has moved to the center of the image, the meaningful feature may be features extracted from the center part of the image.

The first classification module 24-1 and the second classification module 24-2 may combine the extracted features and may classify the extracted features into classes. The first classification module 24-1 and the second classification module 24-2 may be a fully connected layer. The fully connected layer may have multiple layers. The first classification module 24-1 and the second classification module 24-2 may be an identical classification model.

The first classification module 24-1 may combine features extracted by the feature extraction module 23 and classify the extracted features into classes. The second classification module 24-2 may combine features selected by the dimension reduction module 24-3 among the features having been extracted by the feature extraction module 23, and classify the features selected by the dimension reduction module 24-3 into classes.

The adder 24-4 may add outputs of the first classification module 24-1 and the second classification module 24-2. Accordingly, the feature enhancement module 24a according to an exemplary embodiment may obtain an output result, in which the center area is enhanced, by adding features of the entire image, which are output from the first classification module 24-1, and a feature of the center area, which is output from the second classification module 24-2.

Figure 4B:
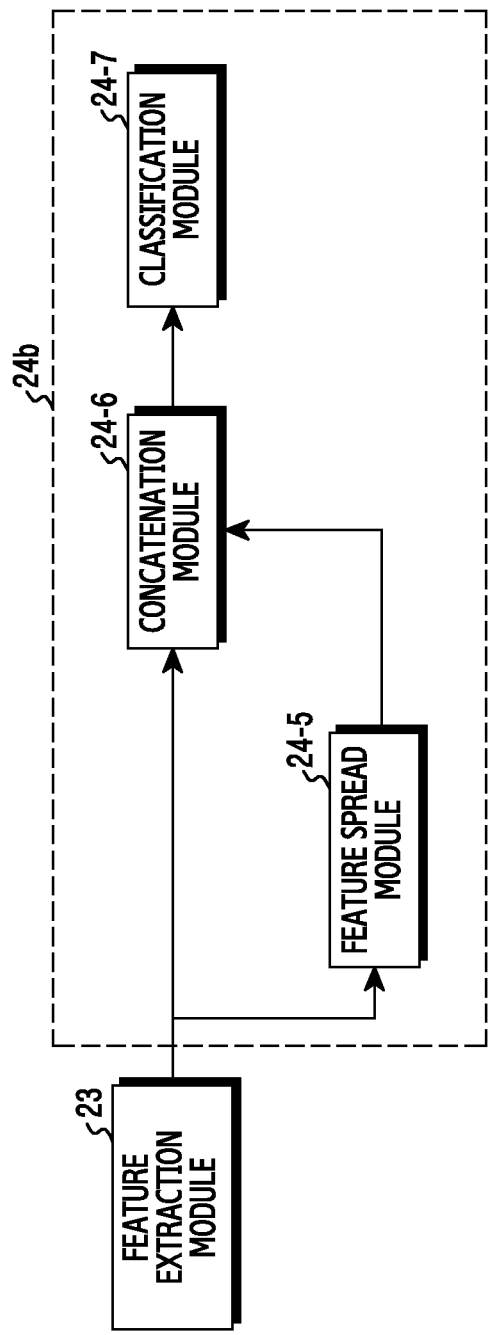
FIG. 4B is a block diagram illustrating a configuration of a feature enhancement module of an electronic device according to another exemplary embodiment.

FIG. 4B is a block diagram illustrating a configuration of a feature enhancement module of an electronic device according to another exemplary embodiment.

Referring to FIG. 4B, the feature enhancement module 24b according to another exemplary embodiment may include a feature spread module 24-5, a concatenation module 24-6, and a classification module 24-7.

The feature spread module 24-5 may spread a feature map output from the feature extraction module 23. For example, the feature spread module 24-5 may increase the size of the feature map and spread a feature, by unpooling the feature map. The feature spread module 24-5 may perform unpooling a plurality of times. For example, when a final output feature map of the feature extraction module 23 has a size of $\frac{1}{32}$ of an original image size, the feature spread module 24-5 may generate a feature map having a size of $\frac{1}{16}$ of the original image size through performing unpooling once. The feature spread module 24-5 may generate a feature map having a size of $\frac{1}{4}$ of the original image size through performing unpooling three times. The feature spread module 24-5 may perform spreading for the entire feature map, and may perform spreading limited to a point or area designated by a user.

The concatenation module 24-6 may concatenate the features output from the feature extraction module 23 and the feature output from the feature spread module 24-5 to enhance a feature of the point or area (e.g., the center area of the image) designated by the user.

The classification module 24-7 may combine the features concatenated by the concatenation module 24-6, and classify the same into classes. The classification module 24-7 may be a fully connected layer.

Figure 4C:
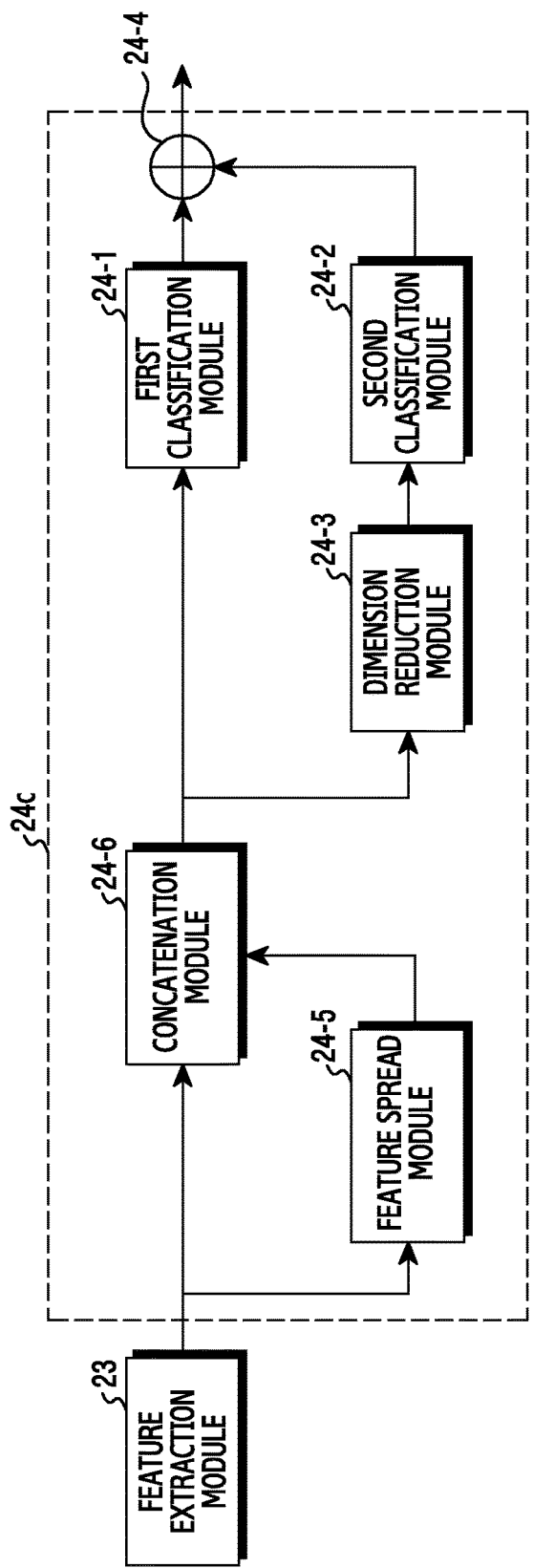
FIG. 4C is a block diagram illustrating a configuration of a feature enhancement module of an electronic device according to still another exemplary embodiment.
Figure 4D:
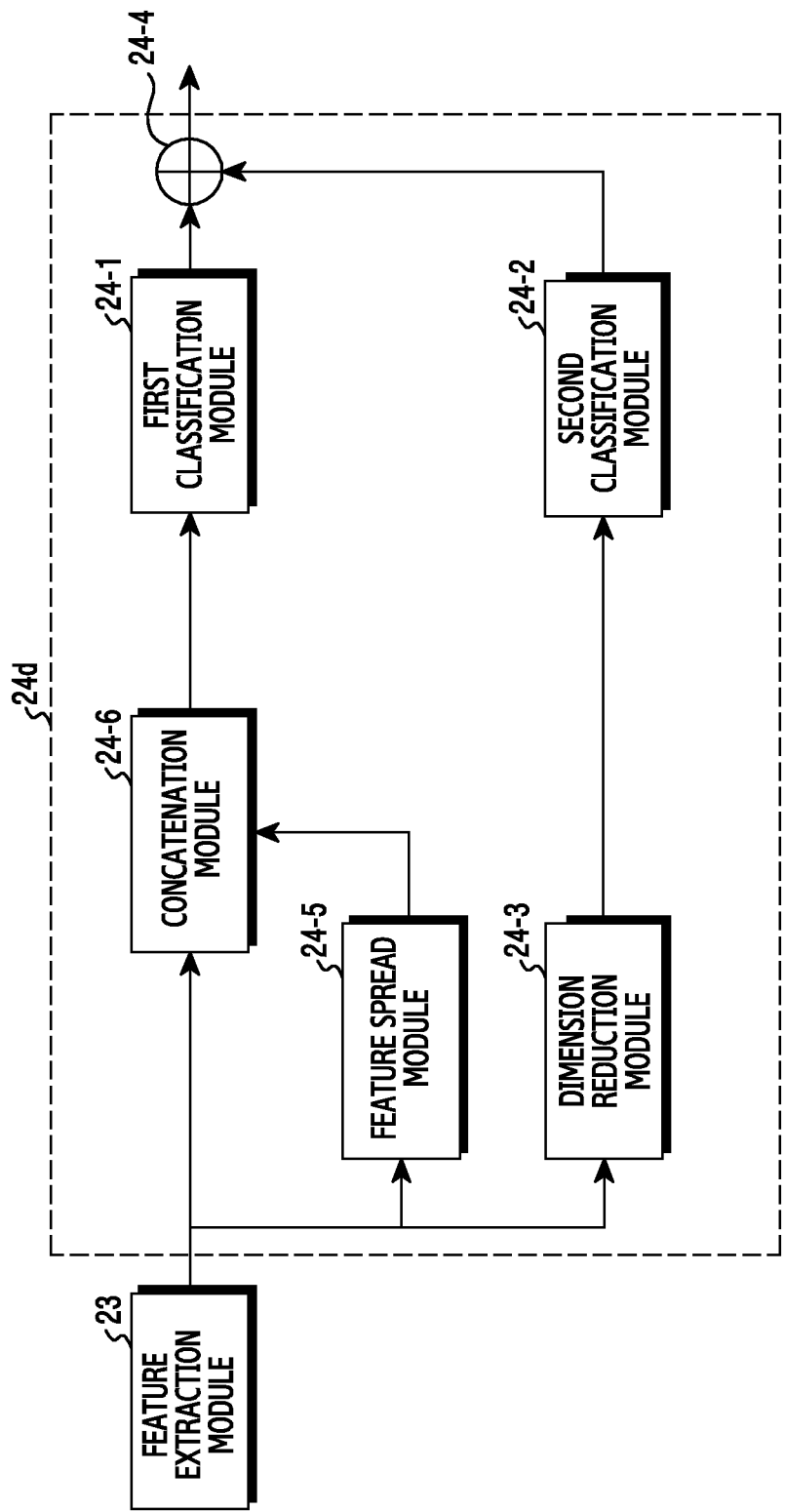
FIG. 4D is a block diagram illustrating a configuration of a feature enhancement module of an electronic device according to still another exemplary embodiment.

FIG. 4C is a block diagram illustrating a configuration of a feature enhancement module of an electronic device according to still another exemplary embodiment, and FIG. 4D is a block diagram illustrating a configuration of a feature enhancement module of an electronic device according to still another exemplary embodiment.

Referring to FIG. 4C and FIG. 4D, feature enhancement modules 24c and 24d according to still another exemplary embodiment may include the first classification module 24-1, the second classification module 24-2, the dimension reduction module 24-3, the adder 24-4, the feature spread module 24-5, and the concatenation module 24-6. For example, the feature enhancement modules 24c and 24d may be formed by combining the feature enhancement modules 24a and 24b of FIG. 4A and FIG. 4B.

First, referring to FIG. 4C, at least one feature extracted by the feature extraction module 23 and a feature spread by the feature spread module 24-5 may be concatenated by the concatenation module 24-6. The first classification module 24-1 may classify the concatenated features into classes, and the dimension reduction module 24-3 may reduce the dimension of the concatenated features. The second classification module 24-2 may classify the features, which have the dimension reduced by the dimension reduction module 24-3, into classes. A result of classification by the first classification module 24-1 and a result of classification by the second classification module 24-2 may be added by the adder 24-4.

Referring to FIG. 4D, at least one feature extracted by the feature extraction module 23 and a feature spread by the feature spread module 24-5 may be concatenated by the concatenation module 24-6. The first classification module 24-1 may classify the concatenated features into classes.

Further, the dimension reduction module 24-3 may reduce the dimension of the at least one feature extracted by the feature extraction module 23. The second classification module 24-2 may classify the feature, which has the dimension reduced by the dimension reduction module 24-3, into classes. A result of classification by the first classification module 24-1 and a result of classification by the second classification module 24-2 may be added by the adder 24-4.

Figure 4E:
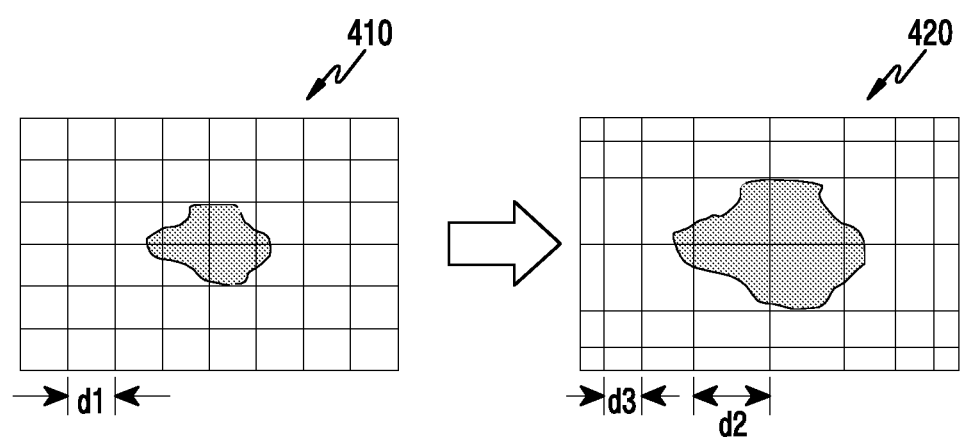
FIG. 4E is a diagram for explaining an image enhancement method of an electronic device according to an exemplary embodiment.

FIG. 4E is a diagram for explaining an image enhancement method of an electronic device according to an exemplary embodiment.

Referring to FIG. 4E, the image enhancement module 22 according to an exemplary embodiment may enlarge the vicinity of the center of a transformed image. For example, the image enhancement module 22 may enlarge the vicinity of the center of the image using an image warping algorithm. In the image before image enhancement, pixels may have a constant interval d1, as illustrated in the drawing of reference numeral 410. On the other hand, in the image to which image enhancement has been applied, it is shown that the interval d2 of pixels near the center of the image increases and the interval d3 of pixels in the outer edge decreases, as illustrated in the drawing of reference numeral 420.

The image enhancement module 22 according to an exemplary embodiment may not be limited to using image warping, and various known techniques may be used.

Figure 5:
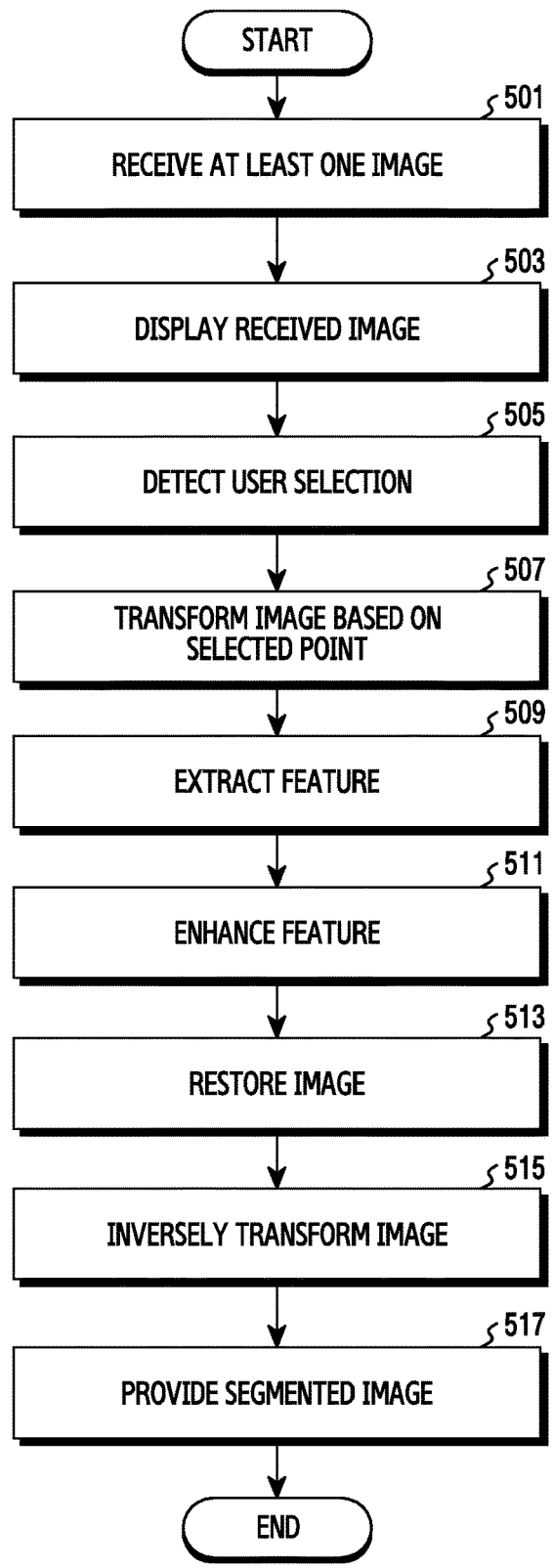
FIG. 5 is a flowchart illustrating an image segmentation method according to an exemplary embodiment.

FIG. 5 is a flowchart illustrating an image segmentation method according to an exemplary embodiment.

Referring to FIG. 5, a processor (e.g., the processor 210 of FIG. 2) of an electronic device (e.g., the electronic device 100 of FIG. 1, and the electronic device 200 of FIG. 2) according to an exemplary embodiment may detect reception (or acquisition) of at least one image, in operation 501. For example, the processor may detect acquisition of a medical image of a patient through a probe (e.g., the probe 150 of FIG. 1, and the probe 250 of FIG. 2).

The processor according to an exemplary embodiment may display the acquired image, in operation 503. For example, the processor may display the acquired image in an area of a display (e.g., the first display 131 and 231, and the second display 132 and 232).

The processor according to an exemplary embodiment may detect a user input that designates a point or an area of the image, in operation 505. For example, the processor may detect a user input that designates a point or an area of the image displayed on the display (e.g., the second display 132 of FIG. 1, and the second display 232 of FIG. 2). The user input may include an input (e.g., a click, a double-click, a click-and-drag, etc.) through a touch input (e.g., a tap, a double-tap, a long touch, a pressure touch, designating a range through dragging, etc.) or a pointing device (e.g., the trackball 160). For example, the user may designate an area of interest (e.g., an area suspected of being a lesion) in the medical image through a touch or a pointing device.

In response to the detection of the user input, the processor according to an exemplary embodiment may transform the image on the basis of the designated point or the designated area, in operation 507. For example, the processor may move the designated point or the designated area to be positioned near the center of the image. In addition, the processor may trim an area that is out of the area of an original image due to the movement. According to an exemplary embodiment, the processor may reduce the size of the moved image to prevent the image from being trimmed.

The processor according to an exemplary embodiment may extract at least one feature from the transformed image, in operation 509. For example, the processor may extract a feature of the image based on various deep learning techniques. For example, the processor may generate a feature map by applying a convolution operation to the transformed image, reduce the size of the feature map through a pooling operation, and apply an activation function. The convolution operation, the pooling operation, and application of the activation function may be performed a plurality of times.

The processor according to an exemplary embodiment may enhance the feature, in operation 511. For example, the processor may enhance at least one feature (e.g., the feature of the center of the image) of the at least one extracted feature. Since the description of feature enhancement of the image has been provided with reference to FIG. 4A to FIG. 4D, a detailed description will be omitted.

The processor according to an exemplary embodiment may restore the image, in operation 513. For example, the processor may restore, as an image, at least one feature of the at least one enhanced feature. Alternatively, the processor may restore, as an image, at least one of the at least one enhanced feature and at least one of the at least one extracted feature. The image restoration may correspond to an operation of restoring the size of the image, which has been reduced in the feature extraction operation, to its original size (resolution). For example, the processor may restore the image through upsampling or deconvolution. The exemplary embodiments are not limited thereto, and the image may be restored through various methods.

The processor according to an exemplary embodiment may inversely transform the restored image, in operation 515. The inverse transformation may correspond to the inverse of operation 507. For example, the processor may move (restore) the center of the image to the point designated in operation 505.

The processor according to an exemplary embodiment may provide segmented images, in operation 517.

When the electronic device is a computer aided diagnosis device, the processor may extract a boundary of the area of interest (e.g., a lesion) and provide the extracted boundary and at least one candidate boundary, based on the segmented images. For example, the processor may display the extracted boundary on the original image displayed on the display (e.g., the first display 131 and 231), and may display the at least one candidate boundary in an area of the display (e.g., the second display 132 and 232). Further, the processor may diagnose the area of interest, and provide (e.g., display) a result of the diagnosis in an area of the display (e.g., the first display 131 and 231).

Figure 6:
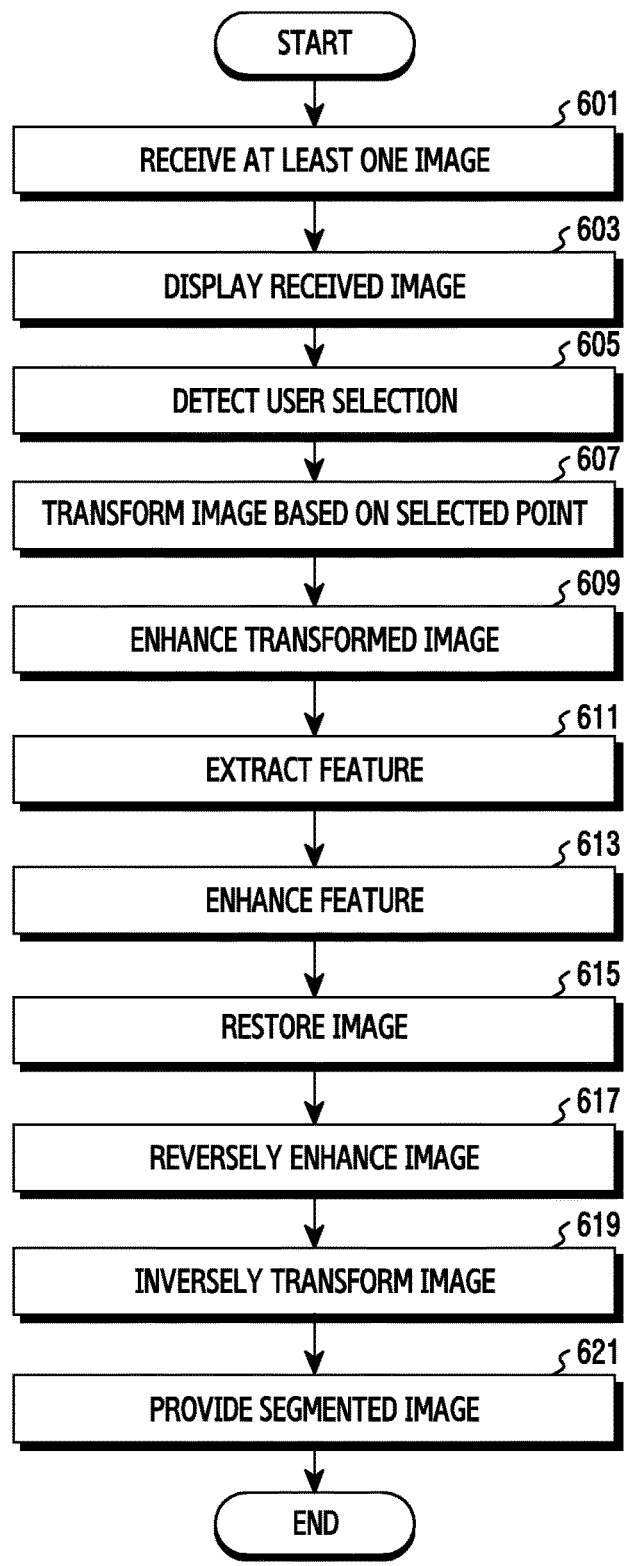
FIG. 6 is a flowchart illustrating an image segmentation method according to another exemplary embodiment.

FIG. 6 is a flowchart illustrating an image segmentation method according to another exemplary embodiment.

Referring to FIG. 6, a processor (e.g., the processor 210 of FIG. 2) of an electronic device (e.g., the electronic device 100 of FIG. 1, and the electronic device 200 of FIG. 2) according to an exemplary embodiment may detect reception (or acquisition) of at least one image, in operation 601. For example, the processor may detect acquisition of a medical image of a patient through a probe (e.g., the probe 150 of FIG. 1, and the probe 250 of FIG. 2).

The processor according to an exemplary embodiment may display the acquired image, in operation 603. For example, the processor may display the acquired image in an area of a display (e.g., the first display 131 and 231, and the second display 132 and 232).

The processor according to an exemplary embodiment may detect a user input that designates a point or an area of the image, in operation 605. For example, the processor may detect a user input that designates a point or an area of the image displayed on the display (e.g., the second display 132 of FIG. 1, and the second display 232 of FIG. 2).

In response to the detection of the user input, the processor according to an exemplary embodiment may transform the image based on the designated point or area, in operation 607. For example, the processor may move the designated point or area to be positioned near the center of the image. In addition, the processor may trim an area that is out of the area of an original image due to the movement. According to an exemplary embodiment, the processor may reduce the size of the moved image to prevent the image from being trimmed.

The processor according to an exemplary embodiment may enhance the transformed image, in operation 609. For example, the processor may increase the size of the center area of the transformed image. Since the description of the image enhancement has been provided, a detailed description will be omitted.

The processor according to an exemplary embodiment may extract at least one feature from the enhanced image, in operation 611. For example, the processor may extract a feature of the image based on various deep learning techniques. For example, the processor may generate a feature map by applying a convolution operation to the transformed image, reduce the size of the feature map through a pooling operation, and apply an activation function. The convolution operation, the pooling operation, and application of the activation function may be performed a plurality of times.

The processor according to an exemplary embodiment may enhance the feature, in operation 613. For example, the processor may enhance at least one feature (e.g., the feature of the center of the image) of the at least one extracted feature. Since the description of feature enhancement of the image has been provided with reference to FIG. 4A to FIG. 4D, a detailed description will be omitted.

The processor according to an exemplary embodiment may restore the image, in operation 615. For example, the processor may restore, as an image, at least one feature of the at least one enhanced feature. Alternatively, the processor may restore, as an image, at least one of the at least one enhanced feature and at least one of the at least one extracted feature. The image restoration may correspond to an operation of restoring the size of the image, which has been reduced in the feature extraction operation, to its original size (resolution). For example, the processor may restore the image through upsampling or deconvolution. The exemplary embodiments are not limited thereto, and the image may be restored through various methods.

The processor according to an exemplary embodiment may perform reverse enhancement of the restored image, in operation 617. The reverse enhancement of the image may correspond to the inverse of operation 609. For example, the processor may restore the image before the enhancement by reversely enhancing the image corresponding to the size of the image enhanced in operation 609.

The processor according to an exemplary embodiment may inversely transform the reversely enhanced image, in operation 619. The inverse transformation may correspond to the inverse of operation 607. For example, the processor may move (restore) the center of the image to the point designated in operation 605.

The processor according to an exemplary embodiment may provide segmented images, in operation 621.

When the electronic device is a computer aided diagnosis device, the processor may provide a boundary of the area of interest (e.g., a lesion) extracted based on the segmented images, at least one candidate boundary, and/or a diagnosis result of the area of interest.

Figure 7:
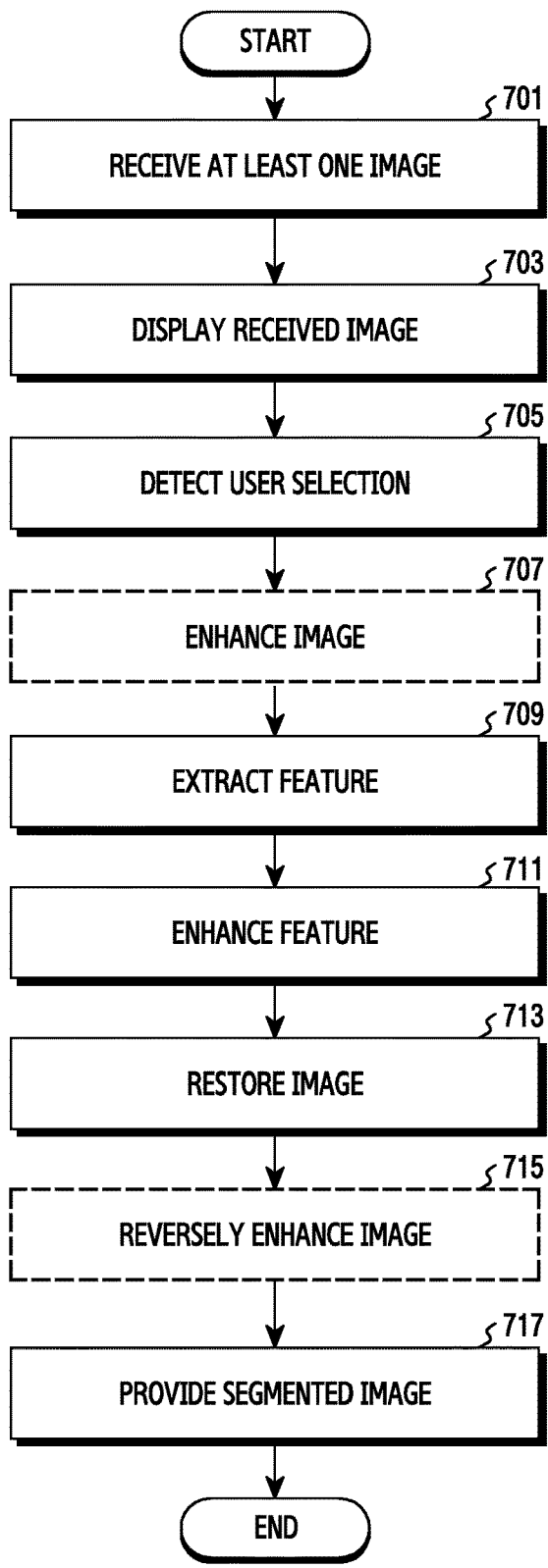
FIG. 7 is a flowchart illustrating an image segmentation method according to still another exemplary embodiment.

FIG. 7 is a flowchart illustrating an image segmentation method according to still another exemplary embodiment.

Referring to FIG. 7, a processor (e.g., the processor 210 of FIG. 2) of an electronic device (e.g., the electronic device 100 of FIG. 1, and the electronic device 200 of FIG. 2) according to an exemplary embodiment may detect reception (or acquisition) of at least one image, in operation 701. For example, the processor may detect acquisition of a medical image of a patient through a probe (e.g., the probe 150 of FIG. 1, and the probe 250 of FIG. 2).

The processor according to an exemplary embodiment may display the acquired image, in operation 703. For example, the processor may display the acquired image in an area of a display (e.g., the first display 131 and 231, and the second display 132 and 232).

The processor according to an exemplary embodiment may detect a user input that designates a point or an area of the image, in operation 705. For example, the processor may detect a user input that designates a point or an area of the image displayed on the display (e.g., the second display 132 of FIG. 1, and the second display 232 of FIG. 2).

The processor according to an exemplary embodiment may enhance the image, in operation 707. For example, the processor may enhance (e.g., increasing the size) an area corresponding to the point (or the area) designated by the user. For example, when the user designates an upper right area of the image, the processor may enhance the upper right area of the image. According to an exemplary embodiment, operation 709 may be omitted.

The processor according to an exemplary embodiment may extract at least one feature from the enhanced image, in operation 709. For example, the processor may extract a feature of the image based on various deep learning techniques. For example, the processor may generate a feature map by applying a convolution operation to the transformed image, reduce the size of the feature map through a pooling operation, and apply an activation function. The convolution operation, the pooling operation, and application of the activation function may be performed a plurality of times.

The processor according to an exemplary embodiment may enhance the feature, in operation 711. For example, the processor may enhance at least one feature (e.g., a feature of the area designated by the user) of the at least one extracted feature. For example, when the user designates an upper right area, the processor may enhance a feature of the upper right area. Since the description of feature enhancement of the image has been provided with reference to FIG. 4A to FIG. 4D, a detailed description will be omitted.

The processor according to an exemplary embodiment may restore the image, in operation 713. For example, the processor may restore an image using at least one feature of the at least one enhanced feature. Alternatively, the processor may restore an image using at least one of the at least one enhanced feature and at least one of the at least one extracted feature. The image restoration may correspond to an operation of restoring the size of the image, which has been reduced in the feature extraction operation, to its original size (resolution). For example, the processor may restore the image through upsampling or deconvolution. The exemplary embodiments are not limited thereto, and the image may be restored through various methods.

The processor according to an exemplary embodiment may perform reverse enhancement of the restored image, in operation 715. The reverse enhancement of the image may correspond to the inverse of operation 707. According to an exemplary embodiment, operation 715 may be omitted. For example, when operation 707 is omitted, operation 715 may be omitted.

The processor according to an exemplary embodiment may provide segmented images, in operation 717.

When the electronic device is a computer aided diagnosis device, the processor may provide a boundary of the area of interest (e.g., a lesion) extracted based on the segmented images, at least one candidate boundary, and/or a diagnosis result of the area of interest.

Figure 8:
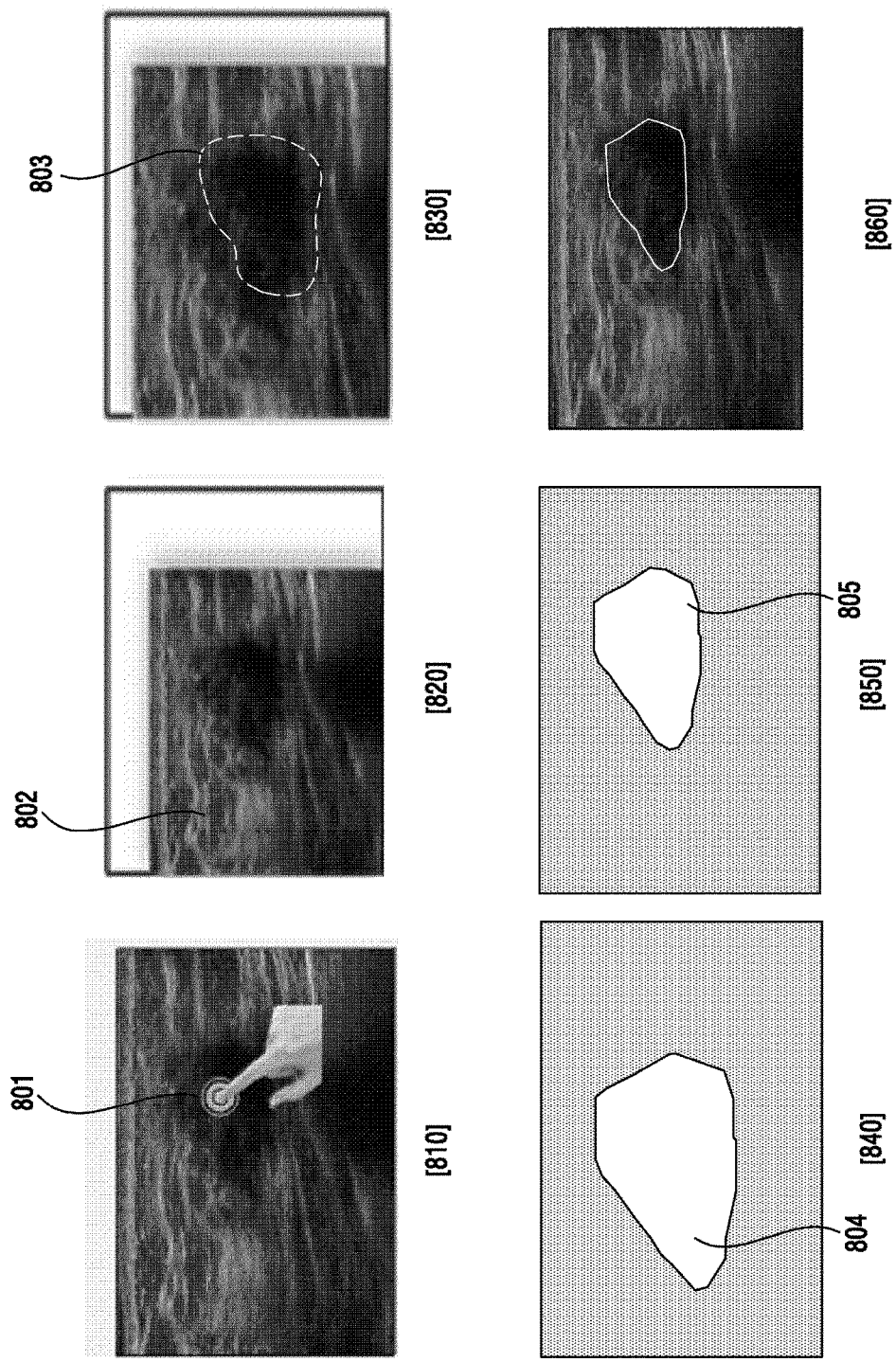
FIG. 8 is a screen illustration diagram for explaining an image segmentation method according to an exemplary embodiment.

FIG. 8 is a screen illustration diagram for explaining an image segmentation method according to an exemplary embodiment.

Referring to FIG. 8, a processor (e.g., the processor 210 of FIG. 2) of an electronic device (e.g., the electronic device 100 of FIG. 1, and the electronic device 200 of FIG. 2) according to an exemplary embodiment may detect a user input 801 that selects a point (e.g., a point in an area suspected of being a lesion) of a medical image, as illustrated in the drawing of reference numeral 810. For example, the user input may be a touch input (e.g., a tap) that designates the point of the medical image. According to an exemplary embodiment, the user input may be a touch gesture input (e.g., a gesture of drawing a circle along an area suspected of being a lesion) that selects the area of the medical image.

When the user input is detected, the processor may move the image such that the touched point is positioned in the center of the image, as illustrated in the drawing of reference numeral 820. The drawing of reference numeral 820 illustrates an example in which the image is moved to the bottom left as the user touches an upper right point with reference to the center of the image. At this time, the moved image 802 may have a trimmed part that is out of the display range of an original image so that the size of the moved image is reduced. According to an exemplary embodiment, the processor may downsize the moved image to prevent the original image from being trimmed.

After the image is moved, the processor may enhance the moved image. For example, the processor may enlarge (increase) the center area 803 of the image, as illustrated in the drawing of reference numeral 830.

When the enhancement of the image is completed, the processor may segment the image using a deep learning algorithm. For example, the processor may extract a feature map by applying a convolution operation to the enhanced image, reduce the size of the feature map by applying a pooling (or subsampling or down sampling) function to the feature map, and applying an activation function (e.g., an ReLU function, a sigmod function, etc.). The processor may enhance the extracted features, and restore the enhanced features as an image. For example, the processor may restore an image by performing upsampling or deconvolution for the enhanced feature.

The restored image may be a first segmentation image divided into an area 804 suspected of being a lesion and the remaining area, as shown in the drawing of reference numeral 840. The processor may perform an image reverse enhancement and an image inverse transformation of the first segmentation image. A second segmentation image, in which the image reverse enhancement and the image inverse transformation are completed, may have the same size and position as those of the image shown in reference numeral 810. For example, the second segmentation image may be downsized by the size of the image, which has been increased by enhancement of the image, and may include a lesion area 805 that is moved from the center to the upper right end, as shown the drawing of reference numeral 850.

The processor may extract a boundary of the lesion based on the second segmentation image, and may display the boundary of the extracted lesion in the original image. For example, the processor may display the boundary of the lesion in a dotted line form in the original image, as illustrated in the drawing of reference numeral 860. This is merely an example and does not limit various exemplary embodiments.

The above description shows that a user selects a seed point in an image. However, various exemplary embodiments are not limited thereto, and the seed point may be selected by the electronic device (e.g., electronic device 100 and the electronic device 200). For example, the electronic device (e.g., electronic device 100 and the electronic device 200) may detect at least one area of interest (e.g., a lesion) through various area detection algorithms from an image currently being input, transform the image such that the at least one detected area of interest is positioned near the center of the image, and then segment the image through the above described method.

According to an exemplary embodiment, when there are a plurality of detected lesions, the electronic device (e.g., the electronic device 100 and the electronic device 200) may check a reliability of each lesion, move a lesion having the highest reliability to near the center of the image, and then segment the image through the described method.

According to other exemplary embodiments, the electronic device (e.g., the electronic device 100 and the electronic device 200) may move at least one lesion, that has a reliability equal to or larger than an designated value (e.g., 65%), among the plurality of lesions to near the center of the screen, and perform image segmentation. At this time, the electronic device (e.g., the electronic device 100 and the electronic device 200) may sequentially perform image segmentation for the plurality of lesions (moving one of the plurality of lesions to the center of the screen to segment the image and then, when the image segmentation is completed, moving another lesion to the center of the screen to segment the image) or may concurrently proceed image segmentation for the plurality of lesions when the electronic device is a multi-processor.

According to various example embodiments, a method for segmenting an image comprising: acquiring an image; displaying the acquired image; detecting selection of a partial area of the displayed image; transforming the image such that the selected partial area is positioned in the center of the image, in response to detection of selection of the partial area of the image; extracting at least one feature from the transformed image, using deep learning; enhancing at least one feature of the at least one extracted feature; restoring, as an image, at least one feature of the at least one enhanced feature; and inversely transforming the restored image to provide segmented images.

According to various exemplary embodiments, the transforming of the image comprises one of: reducing the size of the image by trimming a part out of a display area of the image, the part being generated as the selected partial area is moved to the center of the image; and downsizing the moved image to prevent the image from being out of the display area thereof.

According to various exemplary embodiments, the extracting of the at least one feature comprises repeating a predetermined number of times: generation of a feature map by applying a convolution function to the transformed image, reduction of the size of the feature map by applying a pooling function to the feature map, and application of an activation function.

According to various exemplary embodiments, the enhancing of the at least one feature comprises: a first classification operation configured to classify a class of the at least one extracted feature; a second classification operation configured to reduce a dimension of the extracted feature and classify a class of the dimension-reduced feature; and an operation of adding a result of the first classification operation and a result of the second classification operation.

According to various exemplary embodiments, the enhancing of the at least one feature comprises: combining the at least one extracted feature and at least one feature enhanced by spreading the at least one extracted feature; and classifying a class of the combined feature.

According to various exemplary embodiments, the method may further comprise: enhancing the transformed image; and performing an image reverse enhancement of the restored image.

According to various exemplary embodiments, the enhancing of the image comprises enlarging the center of the transformed image.

According to various exemplary embodiments, the enhancing of the image comprises performing image warping of the transformed image.

According to various exemplary embodiments, the method may further comprise: extracting a boundary based on the segmented images; and displaying the extracted boundary in the acquired image.

According to various exemplary embodiments, the restoring as the image comprises restoring, as an image, at least one of the at least one enhanced feature and at least one of the at least one extracted feature.

According to various example embodiments, a computer-readable storage medium that may store a computer-readable program, wherein the computer-readable program comprises an instruction configured to, when executed by a computer device, cause the computer device to: detect a selection of a partial area of a displayed image; transform the image into a transformed image in which the selected partial area is positioned in a center of the transformed image; extract at least one feature from the transformed image, using deep learning technique; enhance at least one feature corresponding to the partial area of the at least one extracted feature; and restore, as a restored image, at least one feature of the enhanced feature; inversely transform the restored image to provide segmented images.

According to various exemplary embodiments, the instructions further cause the computing device to: enhance the transformed image; and perform an image reverse enhancement of the restored image.

According to various exemplary embodiments, the instructions further cause the computing device to downsize the image to prevent the image from being moved out of a display area when the image is transformed.

According to various exemplary embodiments, the instructions further cause the computing device to trim a part from a display area of the image when the image is transformed, the part being generated by moving the image.

According to various exemplary embodiments, the instructions further cause the computing device to extract the at least one feature by: generating a feature map by applying a convolution function to the transformed image, reducing a size of the feature map by applying a pooling function to the feature map, and applying an activation function.

According to various exemplary embodiments, the instructions further cause the computing device to enhance the at least one feature of the at least one extracted feature by adding a first classification result, in which the at least one extracted feature is classified, and a second classification result, in which the at least one extracted feature is classified by reducing a dimension of the at least one extracted feature.

According to various exemplary embodiments, the instructions further cause the computing device to: create a combined feature by combining the at least one extracted feature and at least one feature enhanced by spreading the at least one extracted feature; and determine a class of the combined feature.

According to various exemplary embodiments, the instructions further cause the computing device to enhance the transformed image by enlarging the center of the transformed image.

According to various exemplary embodiments, the instructions further cause the computing device to: extract a boundary based on the segmented images; and display the extracted boundary in the image.

According to various exemplary embodiments, the instructions further cause the computing device to restore, as the restored image, the at least one enhanced feature and the at least one extracted feature.

Various exemplary embodiments may be able to improve an accuracy of image segmentation as performing the image segmentation by enhancing (image enhancement and/or feature enhancement) a partial area of the image based on a point designated by a user.

The accuracy of a computer diagnosis device according to various exemplary embodiments may be improved in comparison with a computer diagnosis device that divides the image without using existing deep learning and a computer diagnosis device that divides the image by using deep learning without processing the image (e.g., position moving, resizing, image enhancement, and feature enhancement).

The term "module", as used herein, may refer, for example, to a unit including hardware, software, and firmware, or any suitable combination thereof. The term "module" can be interchangeably used with terms such as "unit", "logic", "logical block", "component", "circuit", and the like. A module can be a minimum unit of an integral component or can be a part thereof. A module can be a minimum unit for performing one or more functions or may be a part thereof. A module can be mechanically or electrically implemented. For example, a module, according to an exemplary embodiment, can include, for example, and without limitation, at least one of a dedicated processor, a CPU, an Application-Specific Integrated Circuit (ASIC) chip, a Field-Programmable Gate Arrays (FPGAs), and a programmable-logic device, which are known or will be developed and which perform certain operations.

At least some parts of a device (e.g., modules or functions thereof) or a method (e.g., operations), based on exemplary embodiments, can be implemented with an instruction stored in a non-transitory computer-readable storage medium (e.g., the memory 130) as a program module. When the instruction is executed by a processor (e.g., the processor 120), the processor can perform a function corresponding to the instruction.

The non-transitory computer readable recording medium can include, for example, a hard disk, a floppy disc, a magnetic medium (e.g., a magnetic tape), an optical storage medium (e.g., a Compact Disc-ROM (CD-ROM) or a DVD, a magnetic-optic medium (e.g., a floptical disc)), a flash drive, for example, a compact flash (CF) memory, a secure digital (SD) memory, a micro-SD memory, a mini-SD memory, an extreme digital (xD) memory, a multi-media card (MMC) memory, a memory stick, a USB type memory, or an internal memory. The internal memory may include at least one of a volatile memory (e.g., DRAM, SRAM, SDRAM, or the like), a non-volatile memory (e.g., an OTPROM, a PROM, an EPROM, an EEPROM, a mask ROM, a flash ROM, a flash memory, a hard drive, and a solid-state drive (SSD). The instruction can include code created by a compiler or code executable by an interpreter.

The computer-readable storage medium may download and store a program (or a command) from an external server or an external electronic device. In addition, the computer-readable storage medium may be included in a computer programmable product.

The computer programmable product may store a program for controlling the external electronic device. For example, the computer programmable product may download and store the program from a server, and may be connected to the external electronic device to control the external electronic device (e.g., the electronic device 100 and the electronic device 200). The computer programmable product may be an external memory that can be connected to the electronic device (e.g., the electronic device 100 and the electronic device 200).

The module or program module can further include at least one or more components among the aforementioned components, or can omit some of them, or can further include additional other components. Operations performed by a module, program module, or other components of the various exemplary embodiments can be executed in a sequential, parallel, repetitive, or heuristic manner. In addition, some of the operations can be executed in a different order or may be omitted, or other operations may be added.

The example embodiments disclosed herein and illustrated in the drawings are merely specific examples presented in order to easily describe technical details of the present disclosure and to aid in understanding of the present disclosure, and are not intended to limit the scope of the present disclosure. Therefore, it should be understood that, in addition to the example embodiments disclosed herein, all modifications and changes or modified and changed forms derived from the technical idea of the present disclosure fall within the scope of the present disclosure.

What is claimed is:

1. A non-transitory computer-readable storage medium configured to store a program comprising instructions configured to, when executed by a computing device, cause the computing device to:
   acquire a medical image;
   receive a selection of a partial area of the medical image via an input interface;
   transform the medical image into a transformed medical image in which the selected partial area is positioned in a center of the transformed medical image;
   extract at least one feature from the transformed medical image, using a deep learning technique;
   enhance at least one feature of the at least one extracted feature;
   restore, as a restored medical image, at least one feature of the at least one enhanced feature; and
   inversely transform the restored medical image to provide segmented medical images.

2. The non-transitory computer-readable storage medium of claim 1, wherein the instructions further cause the computing device to:
   enhance the transformed medical image; and
   perform a medical image reverse enhancement of the restored medical image.

3. The non-transitory computer-readable storage medium of claim 1, wherein the instructions further cause the computing device to downsize the medical image to prevent the medical image from being moved out of a display area when the medical image is transformed.

4. The non-transitory computer-readable storage medium of claim 1, wherein the instructions further cause the computing device to extract the at least one feature by:
   generating a feature map by applying a convolution function to the transformed medical image,
   reducing a size of the feature map by applying a pooling function to the feature map, and
   applying an activation function.

5. The non-transitory computer-readable storage medium of claim 1, wherein the instructions further cause the computing device to enhance the at least one feature of the at least one extracted feature by adding a first classification result, in which the at least one extracted feature is classified, and a second classification result, in which the at least one extracted feature is classified by reducing a dimension of the at least one extracted feature.

6. The non-transitory computer-readable storage medium of claim 1, wherein the instructions further cause the computing device to:
   create a combined feature by combining the at least one extracted feature and at least one feature enhanced by spreading the at least one extracted feature; and
   determine a class of the combined feature.

7. The non-transitory computer-readable storage medium of claim 2, wherein the instructions further cause the computing device to enhance the transformed medical image by enlarging the center of the transformed medical image.

8. The non-transitory computer-readable storage medium of claim 1, wherein the instructions further cause the computing device to:
   extract a boundary based on the segmented medical images; and
   display the extracted boundary in the medical image.

9. The non-transitory computer-readable storage medium of claim 1, wherein the instructions further cause the computing device to restore, as the restored medical image, the at least one enhanced feature and the at least one extracted feature.

10. A medical image segmentation method comprising:
    acquiring a medical image;
    displaying the acquired medical image;
    receiving a selection of a partial area of the acquired medical image via an input interface;
    transforming the acquired medical image into a transformed medical image in which the selected partial area is positioned in a center of the transformed medical image;
    extracting at least one feature from the transformed medical image, using a deep learning technique;
    enhancing at least one feature of the at least one extracted feature;
    restoring, as a restored medical image, at least one feature of the at least one enhanced feature; and
    inversely transforming the restored medical image to provide segmented medical images.

11. The method of claim 10, wherein the transforming of the acquired medical image comprises one of:
    reducing a size of the acquired medical image by trimming a part from a display area of the acquired medical image, the part being generated when the selected partial area is moved to the center of the transformed medical image; and
    downsizing the acquired medical image to prevent the acquired medical image from being moved out of the display area.

12. The method of claim 10, wherein the extracting of the at least one feature comprises:
    generating a feature map by applying a convolution function to the transformed medical image,
    reducing a size of the feature map by applying a pooling function to the feature map, and
    applying an activation function.

13. The method of claim 10, wherein the enhancing of the at least one feature comprises:
    a first classification operation comprising determining a class of the at least one extracted feature;
    a second classification operation comprising reducing a dimension of the at least one extracted feature and determining a class of the dimension-reduced feature; and
    adding a result of the first classification operation and a result of the second classification operation.

14. The method of claim 10, wherein the enhancing of the at least one feature comprises:
    creating a combined feature by combining the at least one extracted feature and at least one feature enhanced by spreading the at least one extracted feature; and
    determining a class of the combined feature.

15. The method of claim 10, further comprising:
    enhancing the transformed medical image; and
    performing a medical image reverse enhancement of the restored medical image.

16. The method of claim 15, wherein the enhancing of the transformed medical image comprises enlarging the center of the transformed medical image.

17. The method of claim 10, further comprising:
    extracting a boundary based on the segmented medical images; and
    displaying the extracted boundary in the medical image.

18. The method of claim 10, wherein the restoring comprises restoring, as the restored medical image, the at least one enhanced feature and the at least one extracted feature.

19. An electronic device comprising:
a display configured to display a medical image;
at least one processor operatively connected to the display; and
a memory operatively connected to the at least one processor,
wherein the memory is configured to store instructions which, when executed, cause the processor to:
receive a selection of a partial area of the medical image via an input interface;
extract at least one feature from the displayed medical image, using a deep learning technique;
enhance at least one feature corresponding to the partial area of the at least one extracted feature;
restore, as a restored medical image, at least one feature of the at least one enhanced feature to provide segmented medical images.

20. The non-transitory computer-readable storage medium of claim 1, wherein the instructions further cause the computing device to:
provide one or more boundary candidates of the partial area; and
identify a boundary of the selected partial area based on a selected boundary candidates among the one or more boundary candidates.

21. The method of claim 11, further comprising:
providing one or more boundary candidates of the partial area;
identifying a boundary of the selected partial area based on a selected boundary candidates among the one or more boundary candidates.

22. The electronic device of claim 19, wherein the instructions further cause the processor to:
provide one or more boundary candidates of the partial area; and
identify a boundary of the selected partial area based on a selected boundary candidates among the one or more boundary candidates.

* * * * *